(12) United States Patent  (10) Patent No.: US 6,197,811 B1
Hayes et al.  (45) Date of Patent: Mar. 6, 2001

(54) CYTOKINE PRODUCTION INHIBITORS

(75) Inventors: Martin A. Hayes, Hertfordshire; David J. Hardick, Cambridge; Jenny S. Tang, Worcestershire, all of (GB); Hamish Ryder, Barcelona (ES); Adrian J. Folkes, Buckinghamshire (GB); Toshio Tatsuoka, Hyogo; Masashi Matsui, Osaka, both of (JP)

(73) Assignees: Terragen Discovery Inc., Vancouver (CA); Suntory Limited, Tokyo (JP)

( * ) Notice: Subject to any disclaimer, the term of this patent is extended or adjusted under 35 U.S.C. 154(b) by 0 days.

(21) Appl. No.: 09/292,961

(22) Filed: Apr. 16, 1999

(30) Foreign Application Priority Data

Apr. 17, 1998 (GB) ................................................. 9808196

(51) Int. Cl.$^7$ ......................... A61K 31/35; C07D 309/30

(52) U.S. Cl. ......................... 514/460; 549/292; 549/293

(58) Field of Search ..................................... 549/292, 293; 514/460

(56) References Cited

U.S. PATENT DOCUMENTS

| | | | |
|---|---|---|---|
| 3,701,787 | * 10/1972 | Evans et al. | 260/343.5 |
| 3,909,362 | * 9/1975 | Jiu et al. | 195/81 |
| 5,169,862 | 12/1992 | Burke et al. | 514/450 |

OTHER PUBLICATIONS

George CY Chiou and Shirley XL Liu; "Pulmonary–Allergy, Dermatological, Gastrointestinal & Arthritis", Novel, non–traditional, non–asteroidal, anti–inflammatory agents, Ashley Publications Ltd. ISSN 1354–3776(Exp. Opin. Ther. Patents (1996) 6 (1):41–56).

Stuart B. Krasnoff and Sandeep Gupta; "Identification of the Antibiotic Phomalactone from the Entomopathogenic Fungus Hirsutella–thopsonii VAR synnematosa"; Journal of Chemistry Ecology, vol. 20, No. 2, 1994,293–302.

S. Krivobok, et al.; "6–Allyl–5, 6–dihydro–5–6–dihydro–5–hydroxypyran–2–one, a lactose produced by a new Drechslera species: specified $^1$H and $^{13}$C NMR assignments, mutagenic and immunomodulating testings"; Pharmazie 49 (1994) pp. 605–607.

(List continued on next page.)

Primary Examiner—Amelia Owens
(74) Attorney, Agent, or Firm—Pennie & Edmonds LLP

(57) ABSTRACT

A compound selected from the group consisting of a 5,6-dihydro-α-pyrone of formula (I):

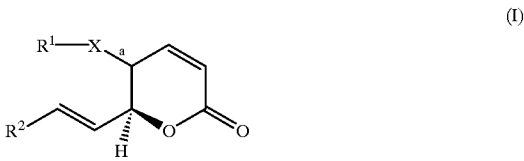

(I)

wherein bond a is oriented either ▶ or ∥∥∥;
X is O or NH;
$R^1$ is selected from the group consisting of:
a group $R^3(O)C$— wherein $R^3$ is selected from the group consisting of: (i) a group of formula $R^4$—CH=CH— wherein $R^4$ is $C_1$–$C_{20}$ alkyl, $C_2$–$C_{20}$ alkenyl, an aryl group,
or a 5- or 6-membered unsaturated heterocyclic ring containing one or two O, N or S atoms, (ii) $C_2$–$C_{20}$ alkyl;
and (iii) an aryl group or a substituent which is a fused ring system of formula (1) or (2):

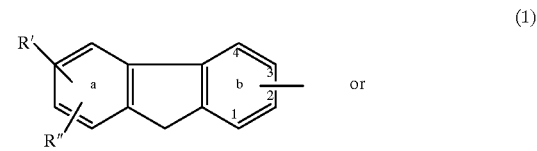

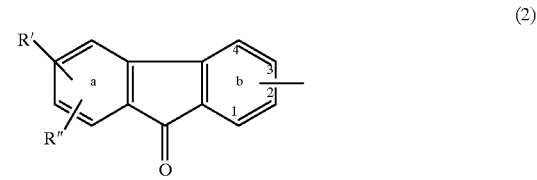

wherein each of R' and R", which are the same or different and may occupy any position on ring a or ring b of said fused ring system, is H or $C_1$–$C_6$ alkyl;
a group $ArCH_2$— wherein Ar is an aryl group; and
a group $R^5O$—$CH_2$— wherein $R^5$ is $C_1$–$C_6$ alkyl optionally interrupted by one or two O atoms; and
$R^2$ is $CH_3$ or, when $R^1$ is a group of formula (A) as defined below, $R^2$ is $R^6OOC$— or $R^6NOC$— wherein $R^6$ is $C_1$–$C_6$ alkyl;
and the pharmaceutically and veterinarily acceptable salts and esters thereof; with the exception of compounds wherein bond a is oriented ▶,
X is O and $R^1$ is a group of formula (A):

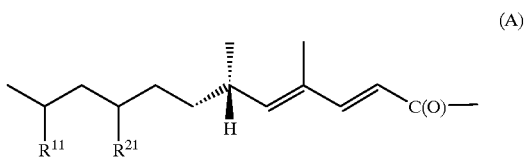

(A)

wherein $R^{11}$ and $R^{21}$ are H when $R^2$ in formula (I) is $CO_2H$ or $CH_3$, or one of $R^{11}$ and $R^{21}$ is H and the other is OH when $R^2$ in formula (I) is $CO_2H$.

13 Claims, No Drawings

OTHER PUBLICATIONS

Maurice V. Laycock, et al.; "Viscosin, a Potent Peptidolipid Biosurfactant and Phytopathogenic Mediator Produced by a Pectolytic Strain of Pseudomonas fluorescens"; J. Agric Food Chem. 1991, 39, 483–489.

E. Loing, A. Delanoye et al.; "Assessing Delivering of Lipo–peptides into the Cytoplasm of Intact Cells by a Functional Assay Based on PKC Inhibition. 1. The Jurkat Model"; Peptide Research vol. 9 No. 5 (1996), 229–232.

McKillop, A., et al.; "The total synthesis of the diepoxycyclohexanone antibiotic aranorosin and novel synthetic analogues"; J. Chem. Soc. Perkin Trans. 1, 1996, 1385–1392.

Tetsuo Toraya, et al.; "Purification and Structural Determination of an Inhibitor of Starfish Oocyte Maturation from a *Bacillus Species*"; Applied and Environmental Microbiology, May 1995, pp. 1799–1804 vol. 61, No. 5.

Peter Wipf, et al.; "Total Synthesis and Structure Assignment of the Antitumor Antibiotic Aranorosin"; J. Org. Chem. 1993, 58, 7195–7203.

Fukushima, T et al "Pyranone and furanone derivatives having herbicidal activity isolated as Microbial metabolities of Nigrospora and preparation of their esters" CA 125:300823 (1996).*

* cited by examiner

CYTOKINE PRODUCTION INHIBITORS

The present invention relates to 5,6-dihydro-α-pyrones useful as cytokine production inhibitors, to the preparation of these compounds and to pharmaceutical and veterinary compositions containing them.

It has been found that a series of synthetic derivatives of phomalactone, a known compound obtainable inter alia by fermentation of a strain of the fungus Phomopsis sp, have activity as inhibitors of cytokine production.

Accordingly the present invention provides a compound which is a 5,6-dihydro-α-pyrone of formula (I):

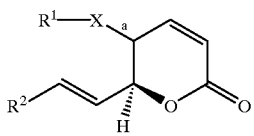
(I)

wherein bond a is oriented either ▶ or ▮▮▮▮;

X is O or NH;

$R^1$ is selected from a group $R^3(O)C$— wherein $R^3$ is either (i) a group of formula $R^4$—CH=CH— wherein $R^4$ is $C_1$–$C_{20}$ alkyl, $C_2$–$C_{20}$ alkenyl, an aryl group or a 5- or 6-membered unsaturated heterocyclic ring containing one or two O, N or S atoms, (ii) $C_2$–$C_{20}$ alkyl, or (iii), an aryl group or a fused ring substituent of formula (1) or (2):

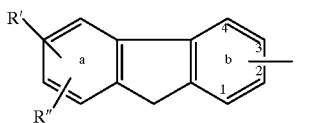
(1)

or

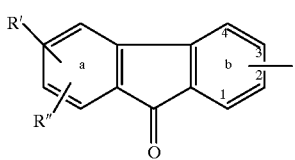
(2)

wherein each of R' and R", which are the same or different and may occupy any position of ring a or ring b of the fused ring system, is H or $C_1$–$C_6$ alkyl;

a group $ArCH_2$— wherein Ar is an aryl group; and a group $R^5O$—$CH_2$— wherein $R^5$ is $C_1$–$C_6$ alkyl optionally interrupted by one or two O atoms; and $R^2$ is $CH_3$ or, when $R^1$ is a group of formula (A) as defined below, $R^2$ is $R^6OOC$— or $R^6NOC$— wherein $R^6$ is $C_1$–$C_6$ alkyl; or a $C_1$–$C_6$ pharmaceutically or veterinarily acceptable salt or ester thereof; with the exception of compounds wherein bond a is oriented ▶, X is O and $R^1$ is a group of formula (A):

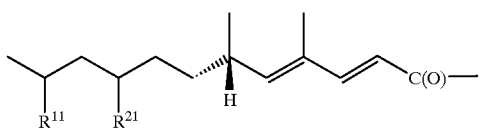
(A)

wherein $R^{11}$ and $R^{21}$ are H when $R^2$ in formula (I) is $CO_2H$ or $CH_3$, or one of $R^{11}$ and $R^{21}$ is H and the other is OH when $R^2$ in formula (I) is $CO_2H$.

In one aspect of the invention the 5,6-dihydro-α-pyrone has the formula (Ia):

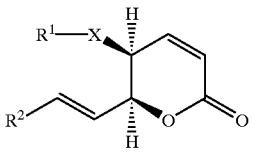
(Ia)

wherein

X is O and $R^1$ is a group $R^3(O)C$—, $ArCH_2$— or $R^5O$—$CH_2$— as defined above, or X is NH and $R^1$ is a group $R^3(O)C$— or $ArCH_2$— as defined above.

In one embodiment of compounds of formula (Ia), X is O and $R^1$ is selected from:

a group $R^3(O)C$— wherein $R^3$ is either (a) a group of formula $R^4$—CH=CH— wherein $R^4$ is naphthyl, furanyl or a phenyl group which is unsubstituted or substituted by $C_1$–$C_6$ alkyl, halo, nitro or hydroxy, (b) a phenyl group which is unsubstituted or para-substitued by $C_1$–$C_6$ alkyl or by phenyl, which phenyl is in turn unsubstituted or substituted by $C_1$–$C_6$ alkyl or $OR^7$ in which $R^7$ is $C_2$–$C_{10}$ alkyl or —$C(O)CH_3$, or (c) a substituent of formula (1a), (2a) or (2b):

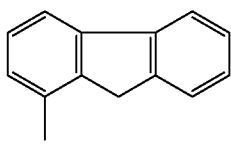
(1a)

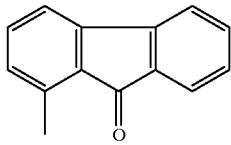
(2a)

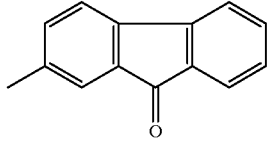
(2b)

and a group $ArCH_2$— wherein Ar is a phenyl group unsubstituted or para-substituted by phenyl, which phenyl is in turn unsubstituted or mono-substituted by $C_1$–$C_6$ alkyl or $OR^7$ as defined above;

or X is NH and $R^1$ is a group $R^3(O)C$— wherein $R^3$ is a phenyl group para-substituted by phenyl, which phenyl is in turn unsubstituted or substituted by $C_1$–$C_6$ alkyl or $OR^7$ as defined above.

In another embodiment of formula (Ia) X is O, $R^1$ is $R^4$—CH═CH—(O)C— wherein $R^4$ is $C_2$–$C_{20}$ alkenyl and $R^2$ is $R^6$OOC— wherein $R^6$ is $C_1$–$C_6$ alkyl. A particularly preferred example of $C_2$–$C_{20}$ alkenyl in this embodiment is the group —CH($CH_3$)═CH—CH($CH_3$)—$(CH_2)_5$—$CH_3$. Preferred examples of $R^6$ in this embodiment are n-propyl and n-butyl.

In a further embodiment of formula (Ia) X is O and $R^1$ is either a group $R^3$(O)C— wherein $R^3$ is a group of formula (2) as defined above or a group $ArCH_2$— wherein Ar is biphenyl.

A preferred group of compounds are those wherein, in formula (Ia), X is O and $R^1$ is selected from:
  a group $R^3$(O)C— wherein $R^3$ is a group of formula (1a), (2a) or (2b) as defined above, a biphenyl, 4-ethyl-biphenyl, 4-pentyl-phenyl or phenylmethyl group, or a group of formula $R^4$—CH═CH— wherein $R^4$ is a naphthyl, furanyl or 3-methylphenyl group; and
  a group $PhCH_2$ wherein Ph is an unsubstituted phenyl group;
  or X is NH and $R^1$ is a group $R^3$(O)C wherein $R^3$ is a biphenyl group.

In another aspect of the invention the 5,6-dihydro-α-pyrone has the formula (Ib):

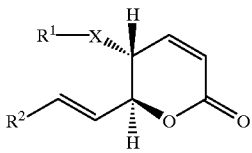

(Ib)

wherein
  X is O and $R^1$ is a group $R^3$(O)C— as defined above, or
  X is —NH and $R^1$ is a group $R^3$(O)C— or $ArCH_2$— as defined above.

In one embodiment of compounds of formula (Ib), X is O and $R^1$ is a group $R^3$(O)C— wherein $R^3$ is a phenyl group which is unsubstituted or substituted by $C_1$–$C_6$ alkyl or $OR^7$ wherein $R^7$ is —C(O)$CH_3$, or X is NH and $R^1$ is a group $R^3$ (O)C— wherein $R^3$ is a phenyl group which is unsubstituted or substituted by phenyl, which phenyl is in turn unsubstituted or substituted by $C_1$–$C_6$ alkyl or $OR^7$ as defined above, or $R^3$ is a substituent of formula (1b):

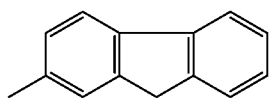

(1b)

A preferred group of compounds are those wherein, in formula (Ib), X is O and $R^1$ is a group $R^3$(O)C— wherein $R^3$ is phenyl, or X is NH and $R^1$ is a group $R^3$(O)C— wherein $R^3$ is biphenyl or a group of formula (1b) as defined above.

An alkyl or alkenyl group may be straight or branched. A $C_1$–$C_6$ alkyl group may be, for example, $C_1$–$C_4$ alkyl such as methyl, ethyl, i-propyl, n-propyl, i-butyl, s-butyl or t-butyl. A $C_1$–$C_{20}$ or $C_2$–$C_{20}$ alkyl group is typically a $C_6$–$C_{18}$, or $C_{10}$–$C_{15}$, alkyl group. A $C_2$–$C_{20}$ alkenyl group is typically a $C_6$–$C_{18}$, or $C_{10}$–$C_{15}$, alkenyl group. An alkoxy group may be straight or branched and may be, for instance, $C_1$–$C_{10}$ alkoxy, for instance $C_2$–$C_{10}$ alkoxy or $C_1$–$C_6$ alkoxy.

An aryl group is typically a $C_6$–$C_{12}$ carbocyclic group containing one or two rings. When two rings are present they may be fused or bonded together. The aryl group is unsubstituted or substituted by one or more substituents. Suitable substituents include alkyl, alkoxy, $OCOR^7$ wherein $R^7$ is alkyl, nitro, hydroxy, and halo groups. Preferred examples of an aryl group are phenyl, naphthyl and biphenyl, each of which is unsubstituted or substituted as defined above.

When the aryl group is phenyl it is typically unsubstituted or substituted by one, two or three substituents selected from $C_1$–$C_6$ alkyl, halo, nitro and hydroxy. $C_1$–$C_6$ alkyl is preferably methyl or ethyl. Halo is preferably bromo or chloro. When $R^4$ is phenyl it is typically unsubstituted or substituted by 2-methyl, 3-bromo, 4-bromo, 2,3,4-trichloro, 2,3,4-trinitro or 2,3,4-hydroxy.

When, in option (iii) for $R^3$ the aryl group is phenyl it is typically either (a) unsubstituted, or (b) substituted by $C_1$–$C_6$ alkyl or by phenyl which is in turn unsubstituted or substituted by $C_1$–$C_6$ alkyl. A phenyl group which is substituted by a $C_1$–$C_6$ alkyl or phenyl substituent is typically mono-substituted. The said substituent may occupy the 2-, 3- or 4-position of the phenyl ring, typically the 3- or 4-position and preferably the 4-position. A phenyl group mono-substituted at the 4-position by a phenyl substituent is a p-biphenyl group. When the phenyl substituent is in turn substituted by $C_1$–$C_6$ alkyl, the alkyl group may occupy the 2-, 3- or 4- position of the phenyl substituent, preferably the 3- or 4-position and more preferably the 4-position.

When the aryl group is naphthyl it is preferably a group of formula (3):

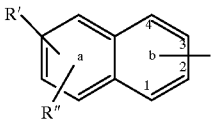

(3)

wherein each of R' and R", which are the same or different and may occupy any position of ring a or ring b of the naphthyl ring system, is H or $C_1$–$C_6$ alkyl.

When the aryl group is biphenyl it is typically unsubstituted or substituted in the second phenyl ring by $C_1$–$C_6$ alkyl or a group —$OCOR^7$ wherein $R^7$ is $C_1$–$C_{10}$ alkyl. When $R^3$ is biphenyl the biphenyl group is preferably unsubstituted or substituted at the 4'-position by $C_1$–$C_6$ alkyl or —$OCOR^7$ as defined above.

When $R^3$ is a $C_2$–$C_{20}$ alkyl group it is, for example, straight or branched chain $C_6$–$C_{18}$ alkyl, suitably straight or branched $C_{10}$–$C_{15}$ alkyl, preferably straight chain $C_{10}$–$C_{15}$ alkyl. When $R^4$ is a $C_1$–$C_{20}$ alkyl group it is, for example, straight or branched $C_6$–$C_{15}$, or $C_6$–$C_{12}$ alkyl. Preferably it is a straight chain alkyl group.

When $R^4$ is a $C_2$–$C_{20}$ alkenyl group it is, for example, straight or branched chain $C_6$–$C_{18}$ alkenyl. The alkenyl chain may contain from 1 to 10 unsaturated bonds, typically from 1 to 4, more preferably 1 or 2 unsaturated bonds. Especially preferred is the group —CH ($CH_3$)═CH—CH ($CH_3$)—$(CH_2)_5$—$CH_3$.

A $C_1$–$C_6$ alkyl group which is interrupted by one or two oxygen atoms is typically an ether or diether group.

A 5- or 6-membered unsaturated heterocyclic ring containing one or two O, N or S atoms is typically selected from furan, thiophene and pyridine. A thiophene ring may in turn be substituted by —CH═CH—COOH.

When, in the group $R^3$(O)C—, $R^3$ is a fused ring substituent of formula (1) or (2) as defined above, or is a naphthyl group of formula (3) as defined above, $R^3$ may be linked to the —C(O) moiety via any of the four free ring positions in ring b. Thus the substituent of formula (1), (2) or (3) may be linked to the —C(O) moiety via position 1, 2, 3 or 4 of ring b, preferably via position 1 or 2.

In formulae (1), (2) and (3) the ring substituents R' and R" may occupy any ring position of each fused ring system. Preferably R' and R" occupy positions in ring a of each formula.

Preferred compounds of the invention are:
- ((2S,3R)-3,6-Dihydro-6-oxo-(2E-prop-1-enyl-2H-pyran-3-yl)) benzoate;
- ((2S,3R)-3,6-Dihydro-6-oxo-(2E-prop-1-enyl-2H-pyran-3-yl))-4-biphenyl carboxylate;
- ((2S,3R)-3,6-Dihydro-6-oxo-(2E-prop-1-enyl-2H-pyran-3-yl))-9-oxo-9H-fluorene carboxylate;
- ((2S,3R)-3,6-Dihydro-6-oxo-(2E-prop-1-enyl-2H-pyran-3-yl))-9-oxo-9H-fluorene-2-carboxylate;
- (5S,6R)-5-benzylamino-6E-prop-1-ene-5,6-dihydro-2H-pyran-2-one;
- (5S,6R)-5-(4-biphenylmethylamino)-6E-prop-1-ene-5,6-dihydro-2H-pyran-2-one;
- (5S,6R)-5-(2-9H-fluorenemethylamino)-6E-prop-1-ene-5,6-dihydro-2H-pyran-2-one;
- ((2S,3R)-3,6-Dihydro-6-oxo-(2E-prop-1-enyl-2H-pyran-3-yl)) phenylamide;
- ((2S,3R)-3,6-Dihydro-6-oxo-(2E-prop-1-enyl-2H-pyran-3-yl))4-biphenylamide;
- ((2S,3R)-3,6-Dihydro-6-oxo-(2E-prop-1-enyl-2H-pyran-3-yl))-9-oxo-9H-fluorene-4-amide;
- ((2S,3R)-3,6-Dihydro-6-oxo-(2E-prop-1-enyl-2H-pyran-3-yl))-4-biphenylamide;
- ((2S,3R)-3,6-Dihydro-6-oxo-(2E-prop-1-enyl-2H-pyran-3-yl))-9-oxo-9H-fluorene-4-amide;
- ((2S,3R)-3,6-Dihydro-6-oxo-(2E-prop-1-enyl-2H-pyran-3-yl))-4-biphenylamide;
- ((2S,3R)-3,6-Dihydro-6-oxo-(2E-prop-1-enyl-2H-pyran-3-yl))2-fluorene-4-amide;
- ((2S,3R)-3,6-Dihydro-6-oxo-(2E-prop-1-enyl-2H-pyran-3-yl))-(2E,4E)-4,6-dimethyldodecanoate;
- (2S,3S)-5-(2-Methoxy-ethoxymethoxy)-6-(2E-prop-1-enyl)-5,6-dihydro-2H-pyran-2-one;
- (2S,3S)-5-(4-Biphenylmethoxy)-6-(2E-prop-1-enyl)-5,6-dihydro-2H-pyran-2-one;
- (2S,3S)-5-Benzyloxy-6-(2E-prop-1-enyl)-5,6-dihydro-2H-pyran-2-one;
- ((2S,3S)-3,6-Dihydro-6-oxo-(2E-prop-1-enyl-2H-pyran-3-yl))dodeca-2E-enoate;
- ((2S,3S)-3,6-Dihydro-6-oxo-(2E-prop-1-enyl-2H-pyran-3-yl))-3-(2-furfuryl)acrylate;
- ((2S,3S)-3,6-Dihydro-6-oxo-(2E-prop-1-enyl-2H-pyran-3-yl))-4-biphenylcarboxylate;
- ((2S,3S)-3,6-Dihydro-6-oxo-(2E-prop-1-enyl-2H-pyran-3-yl))-4'-ethyl-4-biphenylcarboxylate;
- ((2S,3S)-3,6-Dihydro-6-oxo-(2E-prop-1-enyl-2H-pyran-3-yl))-9H-fluorenecarboxylate;
- ((2S,3S)-3,6-Dihydro-6-oxo-(2E-prop-1-enyl-2H-pyran-3-yl))-9-oxo-9H-fluorene carboxylate;
- ((2S,3S)-3,6-Dihydro-6-oxo-(2E-prop-1-enyl-2H-pyran-3-yl))-9-oxo-9H-fluorene-2-carboxylate;
- ((2S,3S)-3,6-Dihydro-6-oxo-(2E-prop-1-enyl-2H-pyran-3-yl))-4-biphenylacetate;
- ((2S,3S)-3,6-Dihydro-6-oxo-(2E-prop-1-enyl-2H-pyran-3-yl))phenylacetate;
- ((2S,3S)-3,6-Dihydro-6-oxo-(2E-prop-1-enyl-2H-pyran-3-yl))-3m-tolylacrylate;
- ((2S,3S)-3,6-Dihydro-6-oxo-(2E-prop-1-enyl-2H-pyran-3-yl))-3-(2-naphthyl)acrylate;
- ((2S,3S)-3,6-Dihydro-6-oxo-(2E-prop-1-enyl-2H-pyran-3-yl))-4-pentylbenzoate;
- ((2S,3S)-3,6-Dihydro-6-oxo-(2E-prop-1-enyl-2H-pyran-3-yl))dodecanoate;
- ((2S,3S)-3,6-Dihydro-6-oxo-(2E-prop-1-enyl-2H-pyran-3-yl))tetradodecanoate;
- ((2S,3S)-3,6-Dihydro-6-oxo-(2E-3-oxo-3-ethoxyprop-1-enyl-2H-pyran-3-yl))-(2E,4E)-4,6-dimethyldodecadienoate;
- ((2S,3S)-3,6-Dihydro-6-oxo-(2E-3-oxo-3-propoxyprop-1-enyl)-2H-pyran-3-yl)-(2E,4E)-4,6-dimethyldodecadienoate;
- ((2S,3S)-3,6-Dihydro-6-oxo-(2E-3-oxo-3-butoxyprop-1-enyl)-2H-pyran-3-yl)-(2E,4E)-4,6-dimethyldodecadienoate;
- ((2S,3S)-3,6-Dihydro-6-oxo-(2E-3-oxo-3-benzylaminoprop-1-enyl)-2H-pyran-3-yl)-(2E,4E)-4,6-dimethyldodecadienoate.

The compounds of the invention are produced by conventional synthetic techniques which start from either phomalactone, which is a compound of the following formula (II):

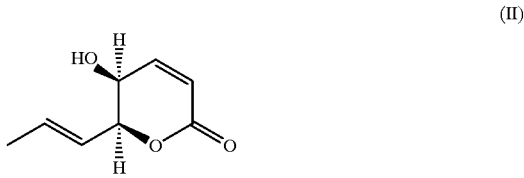

(II)

or the stereoisomer of phomalactone inverted at the 5 position, which is a compound of the following formula (IIa):

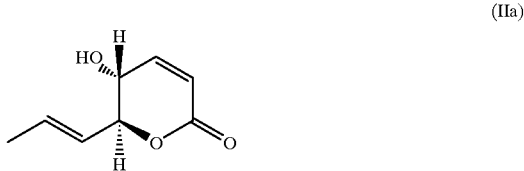

(IIa)

The compound of formula (IIa) may be produced from the compound of formula (II) by the process described in Reference Example 1. The phomalactone of formula (II) is itself known and can be synthesised by methods known in the prior art, for example those disclosed in Krivobok, S, et al, Pharmazie, (1994): 49, H8, 605–607, Guirand, P. et al, Pharmazie (1994): 49, H8, 279–281; Krasnoff, S. B. et al, J. Chem, Ecol., (1994): 20, 293–302 and Murayama, T. et al, Agric. Biol. Chem., (1987): 51, 2055–2060.

The phomalactone of formula (II) may be converted into the corresponding amine inverted at the 5 position, of the following formula (IVa), which is an intermediate in the preparation of compounds of the invention:

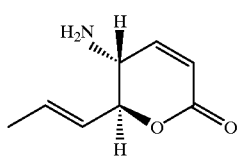

(IVa)

As described in Reference Example 2, this inverted phomalactone amine of formula (IVa) may be obtained by:

(a) treating a phomalactone of formula (II), as defined above, with methanesulphonyl chloride in an organic solvent in the presence of a base to generate the corresponding phomalactone mesylate;

(b) treating the phomalactone mesylate in an organic solvent with sodium azide to produce the corresponding inverted phomalactone azide; and (c) treating a solution of the phomalactone azide in an organic solvent with triphenylphosphine.

In the above step (a) the organic solvent may be, for example, anhydrous dichloromethane. The solution of phomalactone in the organic solvent is typically cooled, for instance to 0° C., prior to addition of the methanesulphonyl chloride. The solution may then be acidified, for instance with an aqueous mineral acid such as HCl, and the organic phase separated off from which phomalactone methanesulphonate is subsequently recovered.

The organic solvent in step (b) is, for example, anhydrous dimethylformamide (DMF). The phomalactone methanesulphonate and sodium azide are added to the organic solvent and typically left to stir, for instance for a period of from 0.5 to 2 hours. Water may be added and the organic phase separated and dried. The inverted phomalactone azide can then be recovered by removal of solvent from the organic phase and purified by conventional techniques, for example by flash chromatography.

In step (c) the organic solvent may be, for example, tetrahydrofuran (THF). The reaction mixture may be stirred, typically at room temperature and suitably for a period of up to 24 hours, following which the solvent may be removed and the resulting crude inverted phomalactone amine of formula (IV) purified by conventional techniques, for instance flash chromatography.

By analogy with the process of Reference Example 2, but starting from the inverted phomalactone of formula (IIa) as defined above, the intermediate amine of the following formula (IV) may be produced:

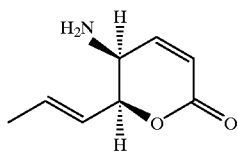

(IV)

This synthesis is described in Reference Example 3.

The invention accordingly further provides a process for producing a 5,6-dihydro-α-pyrone of formula (I), or a salt thereof as defined above, which process comprises:

a) esterifying a compound of formula (II) or (IIa) as defined above with a carboxylic acid of formula (III):

$R^3$—COOH  (III)

wherein $R^3$ is as defined above; or b) treating a compound of formula (IVa) or (IV) as defined above with an aldehyde of formula Ar—CHO wherein Ar is aryl as defined above, or c) treating a compound of formula (IV) or (IVa) as defined above with a carboxylic acid of formula (III) as defined above or an acid chloride of formula $R^3$—COCl wherein $R^3$ is as defined above, where necessary in the presence of a coupling agent, or d) treating a compound of formula (II) or (IIa) as defined above with a halo compound of formula (V):

Ar—$CH_2$Y  (V)

wherein Ar is aryl as defined above and Y is a halogen, or of formula (VI):

$R^5OCH_2Y$  (VI)

wherein $R^5$ is as defined above and Y is a halogen; and e) if desired, converting a 5,6-dihydro-α-pyrone of formula (I) into a pharmaceutically or veterinarily acceptable salt thereof.

Process embodiment (a) gives rise to compounds wherein, in formula (I), X is O and $R^1$ is $R^3(O)C$—, with bond a oriented with either stereochemistry. The carboxylic acids of formula (III) which are used are commercially available compounds. Preferably the reaction is carried out in the presence of a coupling agent such as DCC (dicyclohexylcarbodiimide) or EDC (1-(3-dimethylaminopropyl)-3-ethylcarbodiimide hydrochloride) and dimethylaminopyridine. The reaction is typically carried out in an inert solvent such as dichloromethane or tetrahydrofuran.

The reagents are generally mixed with stirring, for example at a low temperature such as −78° C. The reaction is then allowed to warm to room temperature (20–25° C.) and stirred until complete. The reaction may be monitored chromatographically by thin layer chromatography or reversed phase high performance liquid chromatography (HPLC) and is typically complete within sixteen hours. Other coupling agents such as an alkylchloroformate and triethylamine, phenyldichlorophosphate, 2-chloro-1,3,5-trinitrobenzene and pyridine, and chlorosulfonyl isocyanate can also be used under similar conditions.

Alternatively an excess of the phomalactone of formula (II) can be reacted with the carboxylic acid. The water formed can be removed by azeotropic distillation. Suitable solvents include toluene and 1,4-dioxane. The reaction is typically catalysed by acids such as sulphuric acid and p-toluenesulphonic acid.

In one aspect of process embodiment (a), compounds wherein bond a is oriented ⋯‖ are produced from the phomalactone of formula (II) in the presence of diethyl azodicarboxylate (DEAD) and triphenylphosphine in an organic solvent.

In this process the organic solvent may be, for example, THF or dioxane. The process is suitably conducted by adding a solution of DEAD in the organic solvent to a suspension of the phomalactone, the triphenylphosphine and the carboxylic acid followed by stirring, suitably at room temperature for a period of up to 24 hours. The organic solvent is then removed and the end product purified by conventional techniques, for instance flash chromatography.

Process embodiment (b) gives rise to compounds wherein, in formula (I), X is NH and $R^1$ is a group of formula —$CH_2Ar$ wherein Ar is aryl as defined above for $R^3$. Typically the starting amine is of formula (IVa) and the resulting compound has bond a oriented ⫽⫽⫽.

The reaction of process (b) is typically conducted by mixing together the phomalactone amine and the aldehyde in a solvent such as methanol or acetonitrile. $NaCN(BH_3)$ is then added and the solution adjusted to pH 5-6, for instance by the addition of glacial acetic acid. The solution may then be stirred at room temperature, suitably for a period of 0.5 to 4 hours, after which solvent is removed and the organic residue purified by conventional techniques to yield the desired compounds of formula (I).

Process embodiment (c) gives rise to compounds of the invention wherein X is NH and $R^1$ is a group of formula $R^3(O)C—$. Typically the process is used to produce compounds in which bond a is oriented ⫽⫽⫽ starting from the inverted amine of formula (IVa). Process embodiment (c) is generally conducted in an organic solvent in the presence of a base. Typically the base is added to a solution of the inverted phomalactone amine in the organic solvent. The resulting solution is then cooled, for instance to 0° C., prior to addition of the acid chloride. The reaction mixture may then be stirred, suitably for 0.5 to 2 hours. Water may then be added and the organic phase separated, washed and then reduced to yield the crude product. The residue may then be purified by conventional techniques, for instance flash chromatography.

Process embodiment (d) gives rise to compounds of formula (I) wherein X is O and $R^1$ is a group of formula $ArCH_2—$ or $R^5O—CH_2—$ as defined above. Typically the starting phomalactone is of formula (II) and bond a in the resulting product is oriented ▶. The reaction is generally conducted in an organic solvent in the presence of a Lewis acid.

Depending on the reactants this reaction may be conducted either by dissolving the phomalactone in the solvent and adding thereto the halo compound and Lewis acid, or by dissolving the halo compound in the solvent and adding thereto the phomalactone and Lewis acid. The reaction mixture is typically stirred, for a period of around 4 hours, and suitably at a temperature of about 25° C. The crude residue may be extracted and purified by conventional techniques, for instance flash chromatography.

A compound of the invention wherein $R^1$ is a group of formula (A) as defined above and $R^2$ is $R^6OOC—$ wherein $R^6$ is $C_1-C_6$ alkyl may be produced by esterification of the corresponding free acid, in which $R^2$ is a carboxy group, with an alcohol $R^6OH$ in the presence of a coupling agent. The free acid is obtainable by fermentation of a strain of the fungus *Phomopsis* sp, as described in co-pending application PCT/GB97/02907. The fungal strain was deposited under the Budapest Treaty at the Centraalbureau voor Schimmelcultures, Baarn, the Netherlands, on Mar. 19$^{th}$ 1996 and has been allocated the reference number CBS 313.96.

A 5,6-dihydro-α-pyrone of formula (I) may be converted into pharmaceutically or veterinarily acceptable salt by conventional methods. Suitable salts include salts with alkali metals such as sodium or potassium, and ammonium salts.

The 5,6-dihydro-α-pyrones of formula (I) and the pharmaceutically acceptable and veterinarily acceptable salts thereof are inhibitors of the production of cytokines, specifically IL-1β.

These compounds can therefore be used in the treatment of disorders requiring immunosuppression, for example immunoinflammatory conditions and CNS disorders. A human or animal, e.g. a mammal, can therefore be treated by a method comprising administration of a therapeutically effective amount of a compound of formula (I), or a pharmaceutically or veterinarily acceptable salt of the compound of formula (I) where appropriate.

These compounds can be used in the treatment of an immunoinflammatory condition such as rheumatoid arthritis, osteoarthritis, septic shock, psoriasis, atherosclerosis, inflammatory bowel disease, Crohn's disease and asthma. The compounds of the present invention also exhibit pharmacological properties associated with the treatment of other disorders requiring immunosuppression, for example central nervous system (CNS) disorders such as encephalomyelitis and Alzheimer's disease.

The compounds of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration for adult humans is 0.001 to 10 mg/kg, most commonly in the range of 0.01 to 5 mg/kg, body weight. Such a dosage may be given, for example, from 1 to 5 times daily orally or by bolus infusion, infusion over several hours and/or repeated administration.

The toxicity of the compounds of the invention is negligible. They can therefore safely be used in therapy.

The compounds of the present invention are formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form.

For example, the solid oral forms may contain, together with the active compound, diluents, such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dye-stuffs; sweeteners; wetting agents such as lecithin, polysorbates, laurylsulphates. Such preparations may be manufactured in known manner, for example by means of mixing, granulating, tabletting, sugar coating, or film coating processes.

Liquid dispersions for oral administration may be syrups, emulsions and suspensions. The syrups may contain as carrier, for example, saccharose or saccharose with glycerol and/or mannitol and/or sorbitol. In particular a syrup for diabetic patients can contain as carriers only products, for example sorbitol, which do not metabolise to glucose or which only metabolise a very small amount to glucose. The suspensions and the emulsion may contain as carrier, for example a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution. Alternatively, the compounds of the present invention may be encapsulated within liposomes.

The following examples illustrate the invention.

REFERENCE EXAMPLE 1

Preparation of Compound of Formula (IIa)

To a cold (−40° C.) solution of phomalactone (205 mg, 1.33 mmol) in anhydrous $CH_2Cl_2$ (5 ml) and anhydrous pyridine (0.21 ml, 2.66 mmol) was added trifluoromethane sulfonic anhydride (0.27 ml, 1.6 mmol). The stirring was maintained at −40° C. for 2 h before adding a solution of silver trifluoroacetate (1.47 g, 6.65 mmol) in anhydrous DMF (5 ml). The stirring was maintained at −40° C. for 4 h before adding excess methanol to hydrolyse the inverted trifluoroacetate ester. The reaction mixture was concentrated in vacuo and the residue purified by flash chromatography ($SiO_2$; EtOAc:hexane, 30% to 50%) to afford the inverted (C-5) phomalactone of formula (IIa) (41 mg, 20%) as a pale yellow oil. Further purification by preparative HPLC (C18 Novapak 25 mm×10 cm; isocratic elution of 10% acetonitrile/water; flow rate 14 ml/min; detection at 210 nm) afforded a white solid. $^1H$ NMR ($CDCl_3$) 6.85(1H,dd,J=9.9, 2.4 Hz), 6.02–5.92(2H,m), 5.55(1H,ddq,J=15.4,9.3,1.6 Hz), 4.62(1H,t,J=8.4 Hz), 4.31(1H, dt,J=8.6,2.1 Hz),2.40–2.10 (1H,br.s) and 1.79(3H,dd,J=6.4,1.4 Hz).

REFERENCE EXAMPLE 2

Preparation of Compound of Formula (IVa)

To a solution of phomalactone (152 mg, 0.99 mmol) in anhydrous $CH_2Cl_2$ (5 ml) was added triethylamine (165 μl, 1.18 mmol). The solution was cooled to 0° C. before adding mesyl chloride (91 μl, 1.18 mmol). Stirring was maintained for 20 min before adding aqueous HCl solution (1M, 10 ml). The organic layer was separated off washed (water then saturated $NaHCO_3$ solution), dried ($MgSO_4$) and concentrated in vacuo to give the phomalactone mesylate (200 mg, 87%) as a white solid. $^1H$ NMR ($CDCl_3$) 6.8(1H,dd,J=9.8, 3.9 Hz),6.15(1H,d,J=9.8 Hz),5.95(1H,m),5.45 (1H,m),5.05 (1H,m), 4.9(1H,t,J=5.8 Hz), 3.0(3H,s) and 1.75(3H,d,J=6.0 Hz).

To a solution of the above phomalactone mesylate (200 mg, 0.86 mmol) in anhydrous DMF (4 ml) was added sodium azide (67 mg, 1.03 mmol) and the solution left to stir for 1.5 hrs. Water was then added, the organics were separated and dried ($MgSO_4$). The solvent was removed under reduced pressure to afford a residue which was purified by flash chromatography ($SiO_2$; EtOAc:Hex, 1:3) to afford the corresponding inverted phomalactone azide (141 mg, 51%) as a yellow oil. $^1H$ NMR ($CDCl_3$) 6.75 (1H,dd, J=9.86,3.03 Hz), 6.15(1H,dd,J=9.85,1.85 Hz), 6.0(1H,m), 5.55 (1H,m), 4.75(1H,t, J=7.71 Hz),4.05(1H,m) and 1.75 (3H,m).

To a solution of the inverted phomalactone azide (141 mg, 0.79 mmol) in THF (2 ml) was added distilled water (140 μl) followed by triphenyl phosphine (207 mg, 0.79 mmol). The reaction was stirred at room temperature overnight before removing the solvent under reduced pressure. The residue was purified by flash chromatography ($SiO_2$; $CHCl_3$:MeOH:$NH_3$, 100:10:1) to afford the inverted amine of formula (IVa)(80 mg, 68%) as a yellow oil.

REFERENCE EXAMPLE 3

Preparation of Compound of Formula (IV) (phomalactone amine)

Phomalactone amine was prepared in an analogous manner to that described in Reference Example 2. Hence, inverted phomalactone (54 mg, 0.35 mmol) was converted to the corresponding inverted mesylate (76 mg, 0.32 mmol) and then to the azide (20 mg, 0.11 mmol). This was reduced with triphenylphosphine in aqueous THF to afford the amine (17 mg, 0.11 mmol) which was not purified further.

EXAMPLE 1

((2S,3R)-3,6-Dihydro-6-oxo-(2E-prop-1-enyl-2H-pyran-3-yl)) benzoate

A solution of diethyl azodicarboxylate (DEAD) (57 mg, 0.32 mmol, 0.05 ml) in THF (1 ml) was added dropwise to a stirred suspension of phomalactone (25 mg, 0.16 mmol), triphenylphosphine (86 mg, 0.32 mmol) and benzoic acid (40 mg, 0.32 mmol). The reaction was stirred at room temperature overnight before removing the solvent under reduced pressure. Purification by flash chromatography ($SiO_2$; Hex: EtOAc, 3:1) followed by HPLC afforded the title compound (15 mg, 43%) as a colourless oil.

Examples 1a to 1c were carried out by analogous procedures, but replacing the benzoic acid by other carboxylic acids of formula $R^3$—COOH.

EXAMPLE 1a ((2S,3R)-3,6-Dihydro-6-oxo-(2E-prop-1-enyl-2H-pyran-3-yl))-4-biphenyl carboxylate By replacing benzoic acid with 4-biphenyl carboxylic acid, the title compound was obtained (15 mg, 28%) as a white solid.

EXAMPLE 1b ((2S,3R)-3,6-Dihydro-6-oxo-(2E-prop-1-enyl-2H-pyran-3-yl))-9-oxo-9H-fluorene carboxylate By replacing benzoic acid with 9-fluorenone-2-carboxylic acid and carrying out the reaction in dioxane (1 ml), the title compound was obtained (186 mg, 79%) as a yellow solid.

EXAMPLE 1c ((2S,3R)-3,6-Dihydro-6-oxo-(2E-prop-1-enyl-2H-pyran-3-yl))-9-oxo-9H-fluorene-2-carboxylate By replacing benzoic acid with 9-fluorenone-1-carboxylic acid and carrying out the reaction in 1,4-dioxane (1 ml), the title compound was obtained (42 mg, 60%) as a yellow solid.

EXAMPLE 2a (5S,6R)-5-benzylamino-6E-prop-1-ene-5,6-dihydro-2H-pyran-2-one

Crude inverted phomalactone amine (0.28 mmol), prepared as described in Reference Example 2, was premixed with benzaldehyde (30 mg, 0.28 mmol) in methanol (1 ml) for 10 mins. NaCN($BH_3$) (20 mg,0.32 mmol) was added followed by glacial acetic acid (1 drop) until pH 5–6. After 2 hrs stirring at 20° C., the solution was concentrated in vacuo. The resulting residue was dissolved in $CH_2Cl_2$ before adding saturated $NaHCO_3$ solution . The organic phase was separated off, dried ($MgSO_4$) and concentrated in vacuo. The resulting residue was purified by flash chromatography (SiO2; EtOAc:hexane, 1:1) to afford the title compound (43 mg) as a pale yellow oil.

Examples 2b and 2c were carried out using analogous procedures, but replacing the benzaldehyde by another aldehyde PhCHO.

EXAMPLE 2b (5S,6R)-5-(4-biphenylmethylamino)-6E-prop-1-ene-5,6-dihydro-2H-pyran-2-one Benzaldehyde was replaced with 4-biphenylcarboxaldehyde (51 mg,0.28 mmol). The title compound (29 mg) was obtained as a pale yellow oil.

EXAMPLE 2c (5S,6R)-5-(2-9H-fluorenemethylamino)-6E-prop-1-ene-5,6-dihydro-2H-pyran-2-one Benzaldehyde was replaced with 2-fluorenecarboxaldehyde (55 mg,0.28 mmol). (It was necessary to warm up the initial solution to aid solubilisation). The title compound (27 mg) was obtained as a pale yellow oil.

EXAMPLE 3

((2S,3R)-3,6-Dihydro-6-oxo-(2E-prop-1-enyl-2H-pyran-3-yl)) phenylamide

To a solution of the inverted phomalactone amine of formula (IV) (30 mg, 0.19 mmol), prepared as described in Reference Example 2, in dry $CH_2Cl_2$ (1 ml) was added triethylamine (24 mg, 0.03 ml, 0.23 mmol). The solution was cooled (0° C.) before adding benzoyl chloride (33 mg, 0.03 ml,0.23 mmol) and the stirring maintained for 40 min at 0° C. Water was then added and the organic phase was separated, washed (NaOH then water) then dried ($Na_2SO_4$). The solvent was removed under reduced pressure and the resulting residue purified by flash chromatography ($SiO_2$; EtOAc:Hex, 1:1) to afford the title compound (22 mg, 45%) as a colourless oil.

Examples 3a and 3b were carried out using the above-mentioned synthesis

EXAMPLE 3a ((2S,3R) -3,6-Dihydro-6-oxo- (2E-prop-1-enyl-2H-pyran-3-yl) )4-biphenylamide With the inverted phomalactone amine (86 mg, 0.56 mmol), biphenylcarbonyl chloride (146 mg, 0.67 mmol), triethylamine (68 mg, 0.1 ml, 0.67 mmol) and dry $CH_2Cl_2$ (2 ml). The title compound (97 mg, 52%) was obtained as a colourless oil.

EXAMPLE 3b ((2S,3R)-3,6-Dihydro-6-oxo-(2E-prop-1-enyl-2H-pyran-3-yl))-9-oxo-9H-fluorene-4-amide With the inverted phomalactone amine (33 mg, 0.22 mmol), 9-fluorenone-4-carbonyl chloride (63 mg, 0.26 mmol), triethylamine (26 mg, 0.04 ml, 0.26 mmol) and dry $CH_2Cl_2$ (2 ml). The title compound (33 mg, 43%) was obtained as a colourless oil.

EXAMPLE 3c ((2S,3R)-3,6-Dihydro-6-oxo-(2E-prop-1-enyl-2H-pyran-3-yl))-4-biphenylamide To a cold (0° C.) solution of the phomalactone inverted at the 5 position, prepared as described in Reference Example 1, (41 mg, 0.26 mmol) in $CH_2Cl_2$ (1 ml) and triethylamine (32 mg, 0.04 ml, 0.32 mmol) was added mesyl chloride (37 mg, 0.03 ml, 0.32 mmol) and the reaction stirred for 20 min. Aqueous HCl (1M,10 ml) was then added and the $CH_2Cl_2$ layer was separated off, washed (water then saturated $NaHCO_3$ solution) and dried ($MgSO_4$). Concentration in vacuo followed by flash chromatography (SiO2; EtOAc:hexane, 1:1) afforded the inverted mesylate intermediate (78 mg, 0.34 mmol) as a white solid. $^1$H NMR ($CDCl_3$) 6.8(1H,dd, J=9.84,3.92 Hz), 6.15(1H,d,J=9.86 Hz), 5.95 (1H,m), 5.45(1H,m),5.05(1H,m),4.95(1H,t,J=5.8 Hz),3.05 (3H,s) and 1.7(3H,d,J=6.37 Hz).

To a solution of the above inverted mesylate (78 mg, 0.34 mmol) in anhydrous DMF (iml) was added sodium azide (26 mg, 0.40 mmol) and the reaction mixture stirred for 1.5 hrs at room temperature. Water was then added, the organics were separated then dried ($MgSO_4$). Concentration in vacuo followed by flash chromatography ($SiO_2$; EtOAc:Hex, 1:3) afforded the phomalactone azide (20 mg, 33%) as a yellow oil.

To a solution of the above phomalactone azide (20 mg, 10.1 mmol) in THF (100 $\mu$l) and water (10 $\mu$l) was added triphenyl phosphine (29 mg, 0.11 mmol). The reaction mixture was stirred overnight before being concentrated under reduced pressure. The crude residue (20 mg) obtained was dissolved in anhydrous $CH_2Cl_2$ and the reaction mixture cooled (0° C.) before adding 4-biphenyl carbonyl chloride (34 mg, 0.16 mmol) whilst stirring. On completion (40 min at 0° C.) the solvent was removed under reduced pressure and the residue purified by flash chromatography ($SiO_2$; EtOAc:Hex, 1:1) to afford the title compound (8 mg) as a white solid.

EXAMPLE 3d ((2S,3R)-3,6-Dihydro-6-oxo-(2E-prop-1-enyl-2H-pyran-3-yl))-9-oxo-9H-fluorene-4-amide Following the procedure as described in Example 3c, but replacing 4-biphenyl carbonyl chloride with 9-fluorenone-4-carbonyl chloride, the title compound (5 mg) was obtained as a yellow solid.

EXAMPLE 3e ((2S,3R)-3,6-Dihydro-6-oxo-(2E-prop-1-enyl-2H-pyran-3-yl))-4-biphenylamide Phomalactone amine (17 mg, 0.11 mmol), the compound of formula (IV) prepared in Reference Example 3, was reacted with 4-biphenylcarboxaldehyde (24 mg, 0.13 mmol) in methanol with $NaCN(BH_3)$ (10 mg,0.14 mmol) at pH6.0. This afforded the title compound (5 mg, 0.01 mmol) as a pale yellow oil.

EXAMPLE 3f ((2S,3R) -3,6-Dihydro-6-oxo-(2E-prop-1-enyl-2H-pyran-3-yl))2-fluorene-4-amide Using phomalactone amine (5 mg, 0.03 mmol) replacing 4 -biphenylcarboxaldehyde with 2-fluorenecarboxaldehyde (10 mg, 0.05 mmol). This afforded the title compound (2.8 mg, 0.008 mmol) as a yellow oil.

EXAMPLE 4

((2S,3R)-3,6-Dihydro-6-oxo-(2E-prop-1-enyl-2H-pyran-3-yl))-(2E,4E)-4,6-dimethyldodecanoate To a cold (−78° C.) solution of (6S)-4,6-dimethyldodeca-2E,4E-dienoic acid in anhydrous $CH_2Cl_2$ (2 ml) were added 1-(3-dimethylaminopropyl)-3-ethylcarbodiimide (20 mg, 0.1 mmol) and 4-dimethylaminopyridine (DMAP) (trace) and the reaction stirred for a further 15 min at this temperature. A solution of the inverted phomalactone (15 mg, 0.09 mmol) in anhydrous $CH_2Cl_2$ (2 ml) was added and the reaction warmed to 25° C. Stirring was continued for a further 24 h before concentrating in vacuo. The residue was purified (SiO2; 20% ETOAc:hexane) to afford the title compound (28 mg, 80%) as a clear oil.

EXAMPLE 4a (2S,3S)-5-(2-Methoxy-ethoxymethoxy)-6-(2E-prop-1-enyl)-5,6-dihydro-2H-pyran-2-one To a solution of phomalactone of formula (II) (50 mg,0.32 mmol) in anhydrous $CH_2Cl_2$ (2 ml) was added diisopropylethylamine (300 µl,1.7 mmol) followed by 2-methoxyethoxymethyl chloride (MEM chloride) (180 µl,1.6 mmol). The reaction mixture was stirred at 25° C. for 65 hrs, concentrated in vacuo then purified by flash chromatography (SiO2;EtOAc:hexane,1:1) to give a white solid (59 mg) which was recrystallised ($CH_2Cl_2$/hexane) to give the title compound (40 mg,51%) as fine white needles.

EXAMPLE 4b (2S,3S)-5-(4-Biphenylmethoxy)-6-(2E-prop-1-enyl)-5,6-dihydro-2H-pyran-2-one To a solution of biphenyl methyl iodide (made by refluxing p-phenylbenzylchloride (200 mg, 1 mmol) with NaI (150 mg,1 mmol) in methyl ethyl ketone (10 ml) for 1.5 hrs, then cooling the reaction, discarding the NaCl precipitate before concentrating the filtrate in vacuo to afford biphenyl methyl iodide as a yellow solid) in anhydrous DMF (2 ml) was added silver (I) oxide (82 mg,0.35 mmol) and phomalactone (50 mg,0.32 mmol).

The reaction was stirred at 25° C. for 2.5 hrs, then filtered through Celite. Diethyl ether was added to the filtrate to give a white emulsion which was extracted repeatedly (aqueous HCl (1M) then saturated $NaHSO_3$). The organic phase was dried ($MgSO_4$), filtered then concentrated in vacuo to afford an orange oil. Purification by flash chromatography ($SiO_2$;EtOAc:hexane,10–30%) then HPLC (60% acetonitrile/water; C18 Novapak semi-preparative column 25 mm×20 cm; flow rate 25 ml/min; detection at 250 nm) afforded the title compound (6.6 mg,6%) as a colourless oil.

EXAMPLE 4c (2S,3S)-5-Benzyloxy-6-(2E-prop-1-enyl)-5,6-dihydro-2H-pyran-2-one Benzyl bromide (342 mg,2 mmol) was added to NaI (300 mg,2 mmol) in methyl ethyl ketone (20 ml) and the mixture stirred at 25° C. for 15 min before filtering off the NaBr precipitate. The filtrate was concentrated in vacuo before adding a solution of phomalactone (160 mg,1 mmol) in anhydrous dimethylformamide (2 ml) followed by silver (I) oxide.

The reaction was stirred for a further 4.5 hrs, filtered through Celite and stored overnight in the fridge. Aqueous HCl (1 ml) was then added to give a white emulsion which was worked up ($CH_2Cl_2$, then back-extraction with water and saturated $NaHCO_3$solution). The organic phase was dried ($MgSO_4$), filtered and concentrated. The resulting residue was purified by flash chromatography ($SiO_2$;EtOAc:hexane,10–30%) then HPLC (60% acetonitrile/water; C18 Novapak semi-preparative column 25 mm×20 cm; flow rate 25 ml/min; detection at 210 nm; retention time 5 min.) afforded the title compound (4.6 mg,2%) as a colourless oil.

EXAMPLE 5

((2S,3S)-3,6-Dihydro-6-oxo-(2E-prop-1-enyl-2H-pyran-3-yl))dodeca-2E-enoate

To a cold (−78° C.) and stirred solution of trans-2-dodecanoic acid (25.7 mg, 0.13 mmol), 1-(3-dimethylaminopropyl)-3-ethylcarbodiimide hydrochloride (24.8 mg, 0.13 mmol) and N,N-dimethylaminopyridine (1 mg) in anhydrous $CH_2Cl_2$ (5 ml) was added a solution of phomalactone (20 mg, 0.13 mmol) in anhydrous $CH_2Cl_2$ (2 ml). The reaction mixture was allowed to warm up to 25° C., stirred for a further 16 h at this temperature and then washed (saturated $NH_4Cl$ solution, water then brine). The organic phase was then separated, dried ($MgSO_4$), filtered and concentrated in vacuo. The residue was purified by preparative C18 reverse phase HPLC (20% acetonitrile, water; flow rate 50 ml/min; detection 270 nm; column C18 20 cm×4 cm or 10 cm×25 mm) to afford the title compound (4.0 mg, 23%).

The following Examples 5a to 5m were conducted following the same procedure but replacing trans-2-dodecanoic acid with the relevant carboxylic acid

EXAMPLE 5a ((2S,3S)-3,6-dihydro-6-oxo-(2E-prop-1-enyl-2H-yran-3-yl))-3-(2-furfuryl)acrylate Trans-2-furanacrylic acid (17.9 mg, 0.13 mmol) was used to obtain the title compound (13.8 mg, 39%).

EXAMPLE 5b ((2S,3S)-3,6-Dihydro-6-oxo-(2E-prop-1-enyl-2H-pyran-3-yl))-4-biphenylcarboxylate 4-Biphenylcarboxylic acid (27.7 mg, 0.13 mmol) was used to obtain the title compound (6.6 mg, 15%).

EXAMPLE 5c ((2S,3S)-3,6-Dihydro-6-oxo-(2E-prop-1-enyl-2H-pyran-3-yl))-4'-ethyl-4-biphenylcarboxylate 4'-Ethyl-4-biphenylcarboxylic acid (29.4 mg, 0.13 mmol) was used to obtain the title compound (17.8 mg, 38%).

EXAMPLE 5d ((2S,3S)-3,6-Dihydro-6-oxo-(2E-prop-1-enyl-2H-pyran-3-yl))-9H-fluorenecarboxylate 1-Fluorenecarboxylic acid (27 mg, 0.13 mmol) was used to obtain the title compound (6.6 mg, 15%).

EXAMPLE 5e ((2S,3S)-3,6-Dihydro-6-oxo-(2E-prop-1-enyl-2H-pyran-3-yl))-9-oxo-9H-fluorene carboxylate 9-Fluorenone-1-carboxylic acid (29.1 mg, 0.13 mmol) was used to obtain the title compound (5.2 mg, 11%).

EXAMPLE 5f ((2S,3S)-3,6-Dihydro-6-oxo-(2E-prop-1-enyl-2H-pyran-3-yl))-9-oxo-9H-fluorene-2-carboxylate 9-Fluorenone-2-carboxylic acid (29.1 mg, 0.13 mmol) was used to obtain the title compound (14.7 mg, 31%).

EXAMPLE 5g ((2S,3S)-3,6-Dihydro-6-oxo-(2E-prop-1-enyl-2H-pyran-3-yl))-4-biphenylacetate Biphenylacetic acid (69 mg, 0.32 mmol) was used to obtain the title compound (60 mg, 53%) as a white solid.

EXAMPLE 5h ((2S,3S)-3,6-Dihydro-6-oxo-(2E-prop-1-enyl-2H-pyran-3-yl))phenylacetate Phenylacetic acid was used to obtain the title compound.

EXAMPLE 5i ((2S,3S)-3,6-Dihydro-6-oxo-(2E-prop-1-enyl-2H-pyran-3-yl))-3m-tolylacrylate 3-methyl cinnamic acid was used to obtain the title compound.

EXAMPLE 5j ((2S,3S)-3,6-Dihydro-6-oxo-(2E-prop-1-enyl-2H-pyran-3-yl))-3-(2-naphthyl)acrylate 3-naphthalen-2-yl-acrylic acid was used to obtain the title compound.

EXAMPLE 5k ((2S,3S)-3,6-Dihydro-6-oxo-(2E-prop-1-enyl-2H-pyran-3-yl))-4-pentylbenzoate 4-pentylbenzoic acid was used to obtain the title compound.

EXAMPLE 5l ((2S,3S)-3,6-Dihydro-6-oxo-(2E-prop-1-enyl-2H-pyran-3-yl))dodecanoate Lauric acid was used to obtain the title compound.

EXAMPLE 5m ((2S,3S)-3,6-Dihydro-6-oxo-(2E-prop-1-enyl-2H-20 pyran-3-yl))tetradodecanoate Myristic acid was used to obtain the title compound.

EXAMPLE 6

((2S,3S)-3,6-Dihydro-6-oxo-(2E-3-oxo-3-ethoxyprop-1-enyl-2H-pyran-3-yl))-(2E,4E)-4,6-dimethyldodecadienoate 1-(3-Dimethylaminopropyl)-3-ethylcarbodiimide hydrochloride (16.2 mg, 0.08 mmol) was reacted with 3-((5S,6S)-5,6-dihydro-5-((6S)-4,6-dimethyldodeca-2E, 4E-dienoyl)-2H-pyran-2-on-6-yl)-prop-2E-enoic acid as disclosed in PCT/GB97/02907)(25 mg,0.06 mmol) and N,N-dimethylaminopyridine (2 mg) in the manner described in Example 5. Ethanol (5 mg,0.1 mmol) was added and the reaction allowed to stir at 25° C. for 24 h before work-up. Purification by HPLC (elution initially with 50% acetonitrile:waters increasing this to 100% acetonitrile over 15 min) afforded the title compound (5 mg; 19%)

Examples 6a to 6c were carried out by an analogous procedure, but replacing the ethanol by the appropriate alcohol or amine.

EXAMPLE 6a ((2S,3S)-3,6-Dihydro-6-oxo-(2E-3-oxo-3-propoxyprop-1-enyl)-2H-pyran-3-yl)-(2E,4E)-4,6-dimethyldodecadienoate Replacing ethanol with propanol (5 mg,0.08 mmol) afforded the title compound (4.7 mg; 17%).

EXAMPLE 6b ((2S,3S)-3,6-Dihydro-6-oxo-(2E-3-oxo-3-butoxyprop-1-enyl)-2H-pyran-3-yl)-(2E,4E)-4,6-dimethyldodecadienoate Replacing ethanol with n-butanol (5 mg, 0.07 mmol) afforded the title compound (4.5 mg, 16%).

EXAMPLE 6c ((2S,3S)-3,6-Dihydro-6-oxo-(2E-3-oxo-3-benzylaminoprop-1-enyl)-2H-pyran-3-yl)-(2E,4E)-4,6-dimethyldodecadienoate Replacing ethanol with benzylamine afforded the title compound.

EXAMPLE 7

IL-1 Release from Human Peripheral Blood Mononuclear Cells (PBMC)

The effect of the compounds of the invention on IL-1β release was investigated using a known method (Bakouche, O. et al., (1992), J. Immunol: 148, 84–91). Human peripheral blood mononuclear cells (PBMC) were separated from Buffy coats obtained from normal healthy donors on Lymphoprep. The freshly isolated PBMC were suspended in RPMI 1640 supplemented with 5% FBS and exposed to dose ranges of the compound to be tested followed by the addition of 1 ng/ml LPS. Cells were incubated for 18 hours at 37° C. with 5% $CO_2$ and the cell culture supernatants harvested and stored at −70° C. Effects on the production of IL-1β were determined by using an ELISA.

The compounds of the invention were found to inhibit the release of IL-1β. The compounds were not toxic to PBMC. The $IC_{50}$ ($\mu$M) values for LPS-induced IL-1β production for the 5,6-dihydro-α-pyrones of formula (I) are given in the following Table 1.

TABLE 1

| Example no. | $IC_{50}$ ($\mu$M) |
|---|---|
| 1 | 2.4 |
| 1a | >7.5 |
| 1b | 4.5 |
| 1c | 4 |
| 2a | 12 |
| 2b | 6.9 |
| 2c | 3.6 |
| 3 | 9.7 |
| 3a | 1 |
| 3b | 10 |
| 3c | 1.3 |
| 3d | 11.3 |
| 4 | 4 |
| 4a | 8.5 |
| 4b | 0.4 |
| 4c | 1.2 |
| 5 | 2.8 |
| 5a | 1.2 |

TABLE 1-continued

| Example no. | IC$_{50}$ ($\mu$M) |
|---|---|
| 5b | 0.3 |
| 5c | 0.1 |
| 5d | 0.3 |
| 5e | 0.13 |
| 5f | 1.2 |
| 5g | 13.4 |
| 5h | 1.4 |
| 5i | 1 |
| 5j | 0.7 |
| 5k | 0.4 |
| 5l | 8.4 |
| 5m | 5.4 |
| 6 | 6 |
| 6a | 1.4 |
| 6b | 1.4 |
| 6c | >9 |

EXAMPLE 8

Pharmaceutical Composition

Tablets, each weighing 0.15 g and containing 25 mg of a compound of the invention can be manufactured as follows:

Composition for 10,000 tablets
compound of the invention (250 g)
lactose (800 g)
corn starch (415 g)
talc powder (30 g)
magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

EXAMPLE 9

Physicochemical Characterisation

The compounds prepared in the Examples were characterised by mass spectrometric and proton nmr techniques. The data are set out in the following Table 2.

| | | Mass spec data | | $^1$HNMR data | |
|---|---|---|---|---|---|
| | | Mass (intensity) | | | |
| No | Molecular formula | m/z | mode | Solvent/field | d |
| 1 | C$_{15}$H$_{14}$O$_4$ | MH$^+$ (8%) 259 | DCI + CH$_4$ | CDCl$_3$ | 8.1 (2H, dd, J = 8.39, 1.45 Hz), 7.66 (1H, m), 7.45 (2H, m), 6.99 (1H, dd, J = 9.85, 3.86 Hz), 6.20 (1H dd, J = 9.85, 1 Hz), 5.90 (1H, dqd, J = 15.26, 6.44, 0.95 Hz), 5.55 (2H, m), 5.05 (1H, t, J = 6.15 Hz) and 1.85 (3H, ddd, J = 7.3, <1, <1 Hz) |
| 1a | C$_{21}$H$_{18}$O$_4$ | MH+ (base) 335 | DCI + CH$_4$ | CDCl$_3$ | 8.1 (2H, m), 7.7 (2H, m), 7.6 (2H, m), 7.5 (2H, m), 7.4 (1H, m), 6.9 (1H, dd, J = 9.8, 3.8 Hz), 6.2 (1H, d, J = 9.8 Hz), 5.9 (1H, m), 5.6 (2H, m), 5.1 (1H, t, J = 6.3 Hz) and 1.7 (3H, d, J = 6.4 Hz) |
| 1b | C$_{22}$H$_{16}$O$_5$ | MH+ (40%) 361 | DCI + NH$_3$ | CDCl$_3$ | 8.3–8.2 (2H, m), 7.7–7.4 (5H, m), 6.9 (1H, dd, J = 10, 3 Hz), 6.2 (1H, dd, J = 10, 1 Hz), 5.95 (1H, m), 5.6–5.5 (2H, m), 5.1 (1H, t, J = 7 Hz) and 1.75 (3H, d, J = 6.3 Hz) |
| 1c | C$_{22}$H$_{16}$O$_5$ | MH+ (4%) 360 | DEI | CDCl$_3$ | 7.7–7.35 (7H, m), 7.1 (1H, dd, J = 9.87, 3.81 Hz), 6.2 (1H, dd, J = 9.86, 0.97 Hz), 5.95 (1H, m), 5.6 (1H, m), 5.5 (1H, m), 5.05 (1H, t, J = 6.5 Hz) and 1.7 (3H, d, J = 6.3 Hz) |
| 2 | C$_8$H$_{11}$NO$_2$ | MH$^+$ 154 | DCI + NH$_3$ | CDCl$_3$ | 6.75 (1H, dd, J = 10, 2.34 Hz), 5.95 (1H, dd, J = 10, 2.34 Hz), 5.9 (1H, m), 5.45 (1H, m), 4.35 (1H, t, J = 8.57 Hz), 3.45 (1H, m) and 1.7 (3H, d, J = 6.58 Hz). |
| 2a | C$_{15}$H$_{17}$NO$_2$ | MH+ 244 (base peak) | DCI + CH$_4$ | CDCl$_3$ | 7.36–7.25 (5H, m), 6.84 (1H, dd, J = 9.9, 3.3 Hz), 5.99 (1H, dd, J = 9.9, 1.8 Hz), 5.88 (1H, dqd, J = 15.3, 6.3, <1.0 Hz), 5.52 (1H, ddq, J = 15.3, 7.5, 1.8 Hz), 4.75 (1H, t, J = 7.4 Hz), 3.90 (1H, d, J = 13.3 Hz), 3.86 (1H, d, 13.3 Hz), 3.37 (1H, ddd, J = 7.3, 3.1, 1.6 Hz) and 1.74 (3H, dd, J = 6.3, 1.3 Hz) |
| 2b | C$_{21}$H$_{21}$O$_2$N | MH$^+$ 320 (base peak) | DCI + CH$_4$ | CDCl$_3$ | 7.61–7.55 (4H, m), 7.47–7.32 (5H, m), 6.88 (1H, dd, J = 9.9, 3.2 Hz), 6.02 (1H, dd, J = 9.9, 1.8 Hz), 5.91 (1H, |

-continued

| | | Mass spec data | | ¹HNMR data | |
|---|---|---|---|---|---|
| | | Mass (intensity) | | | |
| No | Molecular formula | m/z | mode | Solvent/field | d |
| | | | | | dqd, J = 15.4, 6.4, <1.0 Hz), 5.55 (1H, ddq, J = 15.4, 7.7, 1.7 Hz), 4.79 (1H, t, J = 7.4 Hz), 3.95 (1H, d, J = 13.3 Hz), 3.91 (1H, d, J = 13.3 Hz), 3.41 (1H, ddd, J = 7.3, 3.1, 1.6 Hz), and 1.76 (3H, dd, J = 6.5, 1.6 Hz) |
| 2c | $C_{22}H_{21}O_2N$ | MH+ 322 (base peak) | DCI + CH$_4$ | CDCl$_3$ | 7.79–7.72 (2H, m), 7.56–7.49 (2H, m), 7.40–7.28 (3H, m), 6.87 (1H, dd, J = 9.9, 3.3 Hz), 6.02 (1H, dd, J = 9.9, 1.6 Hz), 5.90 (1H, dqd, J = 15.3, 6.4, <1.0 Hz), 5.54 (1H, ddq, J = 15.3, 7.4, 1.5 Hz), 4.79 (1H, t, J = 7.4 Hz), 3.97 (1H, d, J = 13.2 Hz), 3.93 (1H, d, J = 13.2 Hz), 3.89 (2H, s), 3.41 (1H, ddd, J = 7.4, 3.1, 1.6 Hz) and 1.77 (3H, dd, J = 6.8, 1.6 Hz) |
| 3 | $C_{15}H_{15}NO_3$ | MH+ 258 (base peak) | DCI + NH$_3$ | CDCl$_3$ | 7.8–7.75 (2H), 7.55–7.45 (1H), 7.45–7.35 (2H), 6.95 (1H, d, J = 8.27 Hz), 6.85 (1H, ddd, J = 9.84, 4.42, 0.73 Hz), 6.1 (1H, dd, J = 9.76, 1.44 Hz), 5.85 (1H, m), 5.55 (1H, m), 4.95 (1H, t, J = 5.83 Hz), 4.85 (1H, m) and 1.75 (3H, d, J = 7.2 Hz). |
| 3a | $C_{21}H_{19}NO_3$ | M 333 | DEI | CDCl$_3$ | 7.90–7.85 (2H, m), 7.70–7.55 (4H, m), 7.50–7.35 (3H, m), 6.95 (1H, d, J = 8.31 Hz), 6.85 (1H, ddd, J = 9.83, 4.42, 0.71 Hz) 6.15 (1H, dd, J = 9.82, 1.43 Hz), 5.9 (1H, m), 5.6 (1H, m), 5.0 (1H, t, J = 6.22 Hz) and 1.75 (3H, d, J = 6.41 Hz). |
| 3b | $C_{22}H_{17}NO_4$ | M 359 | DEI | CDCl$_3$ | 7.75–7.65 (3H, m), 7.45–7.40 (2H, m), 7.35–7.20 (2H, m), 6.9 (1H, dd, J = 9.783, 4.73 Hz), 6.55 (1H, d, J = 7.38 Hz), 6.2 (1H, dd, J = 9.84, 1.22 Hz), 5.95 (1H, m), 5.2 (1H, m), 5.0 (2H, m) and 1.75 (3H, d, J = 6.5 Hz). |
| 3c | $C_{21}H_{19}NO_3$ | M 333 | DEI | CDCl$_3$ | 7.9–7.35 (9H, m), 6.71 (1H, dd, J = 9.52, 5.53 Hz), 6.65 (1H, d, J = 8.74 Hz), 6.2 (1H, d, J = 9.81 Hz), 6.0 (1H, m), 5.6 (1H, m), 5.1 (2H, m) and 1.75 (3H, d, J = 6.92 Hz). |
| 3d | $C_{22}H_{17}NO_4$ | M 359 | DEI | CDCl$_3$ | 7.7–7.2 (7H, m), 7.1 (1H, dd, J = 9.71, 5.69 Hz), 6.65 (1H, d, J = 8.93 Hz), 6.2 (1H, d, J = 9.63 Hz), 6.05 (1H, m), 5.65 (1H, m), 5.05 (2H, m) and 1.7 (3H, d, J = 6.58 Hz). |
| 3e | $C_{21}H_{21}NO_2$ | M+ 319.1573 (24%) | DEI | CDCl$_3$ | 7.3–7.45, 7.55 (9H, m), 6.9 (1H, dd, J = 9.8, 4.75 Hz), 6.05 (1H, d, J = 9.82 Hz) 5.95 (1H, m), 5.8 (1H, m), 4.9 (1H, m), 3.95 (1H, d, J = 13.34 Hz), 3.85 (1H, d, J = 13.32 Hz), 3.45 (1H, m), 1.8 (3H, d, J = 6.36 Hz). |
| 3f | $C_{22}H_{21}O_2N$ | MH$^+$ 332 (cal for $C_{22}H_{21}O_2N$ = 331) | DCI + NH$_3$ | CDCl$_3$, 400 MH$_z$ | 7.78 (1H, d, 7.5), 7.72 (1H, d, 7.8), 7.54 (1H, d, 7.4), 7.49 (1H, s), 7.38 (1H, dd, 6.8, 7.3), 7.32–7.27 (2H, m), 6.89 (1H, dd, 9.8, 4.7), 6.05 (1H, dd, 9.8, 1.2) 5.97 (1H, dqd, 15.4, 6.4, <1), 5.79 (1H, ddq, 15.4, 7.3, 1.5), 4.90 (1H, dd, 7.3, 4.1), 3.95–3.87 (2H, m), 3.49 (1H, dd, 4.1, 4.2), 1.81 (3H, dd, 6.4, 1.0). |
| 4 | $C_{22}H_{32}O_4$ | MH+ 361 (100%) | DCI = CH$_4$ | CDCl$_3$ | 7.35 (1H, d, J = 15.6 Hz), 6.80 (1H, dd, J = 9.9, 4.0 Hz), 6.12 (1H, dd, J = 9.9, 1.2 Hz), 5.90 (1H, dq, J = 15.3, 5.5, 0.9 Hz), 5.78 (1H, d, J = 15.6 Hz), 5.72 (1H, d, J = 10.5 Hz), 5.51 (1H, ddq, J = 15.3, 6.9, 1.7 Hz), 5.41 (1H, m), 4.95 (1H, dd, J = 6.0, 6.1 Hz), 2.56–2.47 (1H, m), 1.79 (3H, m), 1.72 (3H, ddd, J = 7.1, <1, <1 Hz), 1.30–1.20 (10H, m), 0.98 (3H, t, J = 6.6 Hz) and 0.88 (3H, t, J = 7.1 Hz). |

-continued

| No | Molecular formula | Mass spec data Mass (intensity) m/z | mode | ¹HNMR data Solvent/field | d |
|---|---|---|---|---|---|
| 4a | $C_{12}H_{18}O_5$ | M 243 (96%) | CI + $CH_4$ | $CDCl_3$ | 6.98 (1H, dd, J = 9.8, 5.0 Hz), 6.10 (1H, d, J = 9.8 Hz), 5.91 (1H, dqd, J = 15.4, 6.5, <1 Hz), 5.73 (1H, ddq, J = 15.4, 7.4, 1.6 Hz), 4.83 (1H, dd, J = 7.3, 3.4 Hz), 4.79 (1H, d, J = 7.0 Hz), 4.76 (1H, d, J = 7.0 Hz), 4.17 (1H, dd, J = 4.9, 3.5 Hz), 3.76–3.60 (2H, m), 3.56–3.52 (2H, m), 3.37 (3H, s), and 1.77 (3H, dd, J = 6.3, <1 Hz) |
| 4b | $C_{21}H_{20}O_3$ | M 320 (base peak) | DEI | $CDCl_3$ | 7.62–7.33 (9H, m), 6.86 (1H, dd, J = 9.8, 4.9 Hz), 6.12 (1H, dd, J = 9.8, <1 Hz), 5.94 (1H, dqd, J = 16.0, 6.5, <1 Hz), 5.85 (1H, ddq, J = 16.0, 6.8, <1 Hz), 4.88 (1H, dd, J = 6.5, 3.6 Hz), 4.65 (2H, s), 4.15 (1H, dd, J = ~4.0 Hz), and 1.81 (3H, d, J = 6.5 Hz). |
| 4c | $C_{15}H_{16}O_3$ | MH+ 245 (base peak) | DCI + $NH_3$ | $CDCl_3$ | 7.40–7.29 (5H, m), 6.81 (1H, dd, J = 9.9, 4.5 Hz), 6.10 (1H, d, J = 9.8 Hz), 5.90 (1H, dq, J = 15.4, 6.4 Hz), 5.82 (1H, ddq, J = 15.4, 7.2, 1.4 Hz), 4.84 (1H, dd, J = 7.2, 3.9 Hz), 4.60 (2H, s), 4.10 (1H, t, J = 4.1 Hz) and 1.78 (3H, dd, J = 6.1, <1 Hz). |
| 5 | $C_{20}H_{30}O_4$ | M + $NH_4$+ 352 (base peak) MH+ 335 (88%) | DCI + $NH_3$ | $CDCl_3$ | 7.03 (1H, dt, J = 15.6, 7.0 Hz), 6.98 (1H, dd, J = 9.8, 5.4 Hz), 6.20 (1H, d, J = 9.7 Hz), 5.95 (1H, dqd, J = 15.3, 6.4, <1.0 Hz), 5.82 (1H, dt, J = 15.6, 1.5 Hz), 5.62 (1H, ddq, J = 15.3, 7.3, 1, 6 Hz), 5.30 (1H, dd, J = 5.4, 3.2 Hz), 4.97 (1H, m), 2.22 (2H, qd, J = 7.1, 1.4 Hz), 1.78 (3H, dd, J = 6.9, 1.3 Hz), 1.50–1.25 (14H, m) and 0.89 (3H, t, J = 6.7 Hz) |
| 5a | $C_{15}H_{14}O_5$ | m/z 274 (<5%) m/z 121 $[C_7H_5O_2]^{+*}$ (base peak) | LCMS (thermospray) | $d_4$-MeOH | 7.72 (1H, m), 7.60 (1H, d, J = 15.7 Hz), 7.21 (1H, dd, J = 9.7, 5.6 Hz), 6.89 (1H, d, J = 3.4 Hz), 6.62 (1H, dd, J = 3.4, 1.8 Hz), 6.35 (1H, d, J = 15.7 Hz), 6.30 (1H, d, J = 9.7 Hz), 6.14–6.03 (1H, m), 5.79–5.69 (1H, m), 5.51 (1H, dd, J = 5.5, 3.0 Hz), 5.21–5.18 (1H, m) and 1.82 (3H, dd, J = 6.3, <1.0 Hz) |
| 5b | $C_{21}H_{18}O_4$ | m/z 334 (<5%) m/z 181 $[C_9H_9O_4]^{+*}$ (base peak) | LCMS (thermospray) | $CDCl_3$ | 8.12–8.08 (2H, m), 7.71–7.66 (2H, m), 7.64–7.61 (2H, m), 7.50–7.45 (2H, m), 7.44–7.38 (1H, m), 7.10 (1H, dd, J = 9.8, 5.4 Hz), 6.27 (1H, d, J = 9.6 Hz), 6.02 (1H, dqd, J = 15.3, 6.8, <1.0 Hz), 5.73 (1H, ddq, J = 15.3, 7.2, 1.5 Hz), 5.51 (1H, dd, J = 5.5, 3.0 Hz), 5.08 (1H, m) and 1.76 (3H, dd, J = 6.8, 1.2 Hz) |
| 5c | $C_{23}H_{22}O_4$ | MH+ 363 (base peak) | DCI + $NH_3$ | $CDCl_3$ | 8.10–8.05 (2H, m), 7.69–7.65 (2H, m), 7.57–7.53 (2H, m), 7.32–7.28 (2H, m), 7.09 (1H, dd, J = 9.7, 5.4 Hz), 6.27 (1H, d, J = 9.6 Hz), 6.01 (1H, dqd, J = 15.4, 6.5, <1.0 Hz), 5.72 (1H, ddq, J = 15.4, 7.3, 1.6 Hz), 5.51 (1H, dd, J = 5.5, 3.1 Hz), 5.06 (1H, dd, J = 7.3, 2.7 Hz), 2.72 (2H, q, J = 7.6 Hz), 1.75 (3H, d, J = 6.4 Hz) and 1.29 (3H, t, J = 7.7 Hz) |
| 5d | $C_{22}H_{18}O_4$ | m/z 346 (9%) m/z 193 (base peak) | LC-MS (thermospray) | $CDCl_3$ | 8.03–7.97 (2H, m), 7.81 (1H, dd, J = 6.9, <1.0 Hz), 7.61 (1H, dd, J = 7.4, <1.0 Hz), 7.49 (1H, dd, J = 7.8, 7.7 Hz), 7.43–7.34 (2H, m), 7.15 (1H, dd, J = 9.6, 5.5 Hz), 6.29 (1H, d, J = 9.8 Hz), 6.05 (1H, dqd, J = 15.3, 6.4, <1.0 Hz), 5.74 (1H, J = 15.5, 7.2, 1.8 Hz), 5.57 (1H, dd, J = 5.5, 3.0 Hz), 5.13–5.09 (1H, m), 4.22 (2H, s) and 1.75 (3H, dd, J = 6.3, 1.0 Hz) |

-continued

| No | Molecular formula | Mass spec data Mass (intensity) m/z | mode | ¹HNMR data Solvent/field | d |
|---|---|---|---|---|---|
| 5e | $C_{22}H_{16}O_5$ | m/z 361 (MH+, 11%) m/z 378 (M + $NH_{4+,\text{ base peak}}$) | DCI + $NH_3$ | $CDCl_3$ | 7.68–7.64 (2H, m), 7.56–7.48 (3H, m), 7.39 (1H, dd, J = 7.9, <1.0 Hz), 7.33 (1H, td, J = 7.3, 1.4 Hz), 7.19 (1H, dd, J = 9.6, 5.1 Hz), 6.29 (1H, d, J = 9.7 Hz), 5.99 (1H, dqd, J = 15.3, 6.4, <1.0 Hz), 5.70 (1H, ddq, J = 15.3, 6.9, 1.5 Hz), 5.63 (1H, dd, J = 5.2, 3.3 Hz), 5.11–5.08 (1H, m) and 1.78–1.74 (3H, ddd, J = 6.4, 1.1, <1.0 Hz) |
| 5f | $C_{22}H_{16}O_5$ | m/z 361 (MH+, 12%) m/z 378 (M + $NH_4$+, base peak) | DCI + $NH_3$ | $CDCl_3$ | 8.27 (1H, d, J = 1.1 Hz), 8.18 (1H, dd, J = 7.7, 1.5 Hz), 7.71 (1H, d, J = 7.3 Hz), 7.64–7.52 (3H, m), 7.39 (1H, td, J = 7.4, <1.0 Hz), 7.08 (1H, dd, J = 9.7, 5.4 Hz), 6.28 (1H, d, J = 9.7 Hz), 6.01 (1H, dqd, J = 15.3, 6.5, <1.0 Hz), 5.69 (1H, ddq, J = 15.3, 7.3, 1.6 Hz), 5.51 (1H, dd, J = 5.4, 3.1 Hz), 5.10–5.06 (1H, m) and 1.73 (3H, dd, J = 6.3, <1.0 Hz). |
| 5g | $C_{22}H_{20}O_4$ | MS 348 (20%) | DEI | $CDCl_3$ | 7.59–7.54 (4H, m), 7.46–7.41 (2H, m), 7.37–7.32 (3H, m), 6.94 (1H, dd, J = 9.7, 5.4 Hz), 6.20 (1H, d, J = 9.7 Hz), 5.87 (1H, dqd, J = 15.3, 6.4, <1.0 Hz), 5.45 (1H, ddq, J = 15.3, 7.2, 1.5 Hz), 5.26 (1H, dd, J = 5.5, 3.1 Hz), 4.92 (1H, m), 3.60 (2H, s) and 1.64 (3H, dd, J = 6.3, 1.1 Hz) |
| 5h | $C_{16}H_{16}O_4$ | m/z 272 (<5%) m/z 91 $[C_7H_7]^+$ (base peak) | LCMS | $CDCl_3$ | 7.36–7.25 (5H, m), 6.92 (1H, dd, J = 9.6, 5.5 Hz), 6.19 (1H, d, J = 9.7 Hz), 5.85 (1H, dqd, J = 15.3, 6.5, <1.0 Hz), 5.41 (1H, ddq, J = 15.3, 7.2, 1.5 Hz), 5.23 (1H, dd, J = 5.5, 3.1 Hz), 4.92–4.89 (1H, m), 3.65 (2H, s) and 1.64 (3H, dd, J = 6.2, 1.2 Hz) |
| 5i | $C_{18}H_{18}O_4$ | m/z 298 (<5%) m/z 145 $[C_{10}H_9O]^{+*}$ (base peak) | LC-MS (thermospray) | $CDCl_3$ | 7.69 (1H, d, J = 16.0 Hz), 7.37–7.32 (2H, m), 7.29 (1H, t, J = 7.4 Hz), 7.24–7.21 (1H, m), 7.02 (1H, dd, J = 9.7, 5.4 Hz), 6.42 (1H, d, J = 15.9 Hz), 6.23 (1H, d, J = 9.7 Hz), 5.97 (1H, dqd, J = 15.5, 6.5, <1.0 Hz), 5.66 (1H, ddq, J = 15.5, 7.3, 1.8 Hz), 5.38 (1H, dd, J = 5.4, 3.0 Hz), 4.99 (1H, dd, J = 7.3, 3.0 Hz), 2.38 (3H, s) and 1.76 (3H, dd, J = 6.6, 1.3 Hz) |
| 5j | $C_{21}H_{18}O_4$ | m/z 334 (9%) m/z 181 $[C_{13}H_{10}O]^{+*}$ (base peak) | LC-MS (thermospray) | $CDCl_3$ | 7.96 (1H, br.s), 7.91–7.82 (4H, m), 7.67 (1H, dd, J = 8.5, 1.6 Hz), 7.56–7.50 (2H, m), 7.04 (1H, dd, J = 9.7, 5.5 Hz), 6.55 (1H, d, J = 15.9 Hz), 6.25 (1H, d, J = 9.6 Hz), 5.99 (1H, dqd, J = 15.3, 6.5, <1.0 Hz), 5.69 (1H, ddq, J = 15.3, 7.3, 1.6 Hz), 5.41 (1H, dd, J = 5.5, 3.0 Hz), 5.02 (1H, dd, J = 7.2, 2.9 Hz) and 1.78 (3H, dd, J = 6.45, 1.2 Hz) |
| 5k | $C_{20}H_{24}O_4$ | m/z 175 $[C_{12}H_{15}O]^{+*}$ (base peak) | LC-MS (thermospray) | $CDCl_3$ | 7.96–7.91 (2H, m), 7.28–7.23 (2H, m), 7.06 (1H, dd, J = 9.8, 5.4 Hz), 6.24 (1H, d, J = 9.8 Hz), 5.98 (1H, dqd, J = 15.2, 6.5, <1.0 Hz), 5.69 (1H, ddq, J = 15.2, 7.4, 1.5 Hz), 5.45 (1H, dd, J = 5.5, 3.1 Hz), 5.06–5.01 (1H, m), 2.67 (2H, t, J = 7.6 Hz), 1.72 (3H, dd, J = 6.3, 1.2 Hz), 1.68–1.59 (2H, m), 1.40–1.28 (4H, m) and 0.89 (3H, t, J = 7.0 Hz) |
| 5l | $C_{20}H_{32}O_4$ | m/z 337 (MH+, 23%) m/z 354 (M + $NH_4$+, base peak) | DCI + $NH_3$ | $CDCl_3$ | 6.98 (1H, dd, J = 9.7, 5.4 Hz), 6.19 (1H, d, J = 9.7 Hz), 5.94 (1H, dqd, J = 15.3, 6.5, <1.0 Hz), 5.58 (1H, ddq, J = 15.3, 7.2, 1.6 Hz), 5.24 (1H, dd, J = 5.4, 3.1 Hz), 4.94 (1H, dd, J = 7.2, 3.1 Hz), 2.32 (2H, t, J = 7.4 Hz), 1.76 (3H, dd, J = 6.4, 1.2 Hz), 1.65–1.56 (2H, m), 1.32–1.22 (16H, m) and 0.88 (3H, t, J = 7.1 Hz) |

-continued

| | | Mass spec data | | $^1$HNMR data | |
|---|---|---|---|---|---|
| | | Mass (intensity) | | | |
| No | Molecular formula | m/z | mode | Solvent/field | d |
| 5m | $C_{22}H_{36}O_4$ | m/z 365 (MH+, 23%) m/z 382 (M + NH$_4$+, base peak) | DCI + NH$_3$ | CDCl$_3$ | 6.92 (1H, dd, J = 9.6, 5.5 Hz), 6.19 (1H, d, J = 9.7 Hz), 5.93 (1H, dqd, J = 15.3, 6.5, <1.0 Hz), 5.59 (1H, ddq, J = 15.3, 7.2, 1.5 Hz), 5.24 (1H, dd, J = 5.5, 3.1 Hz), 4.96–4.91 (1H, m), 2.32 (2H, t, J = 7.4 Hz), 1.75 (3H, dd, J = 6.7, 1.2 Hz), 1.65–1.56 (2H, m), 1.32–1.22 (20H, m) and 0.88 (3H, t, J = 7.0 Hz) |
| 6 | $C_{24}H_{34}O_6$ | m/z 418, M + <5% | LC-MS (thermospray) | CDCl$_3$ | 7.30 (1H, d, J = 15.7 Hz), 7.01 (1H, dd, J = 9.8, 5.3 Hz), 6.89 (1H, dd, J = 15.7, 4.7 Hz), 6.30 (1H, dd, J = 15.7, 1.9 Hz), 6.22 (1H, d, J = 9.8 Hz), 5.75 (1H, d, J = 15.4 Hz), 5.74 (1H, d, J = 10 Hz), 5.49 (1H, dd, J = 5.3, 3.4 Hz), 5.25–5.22 (1H, m), 4.21 (2H, q, J = 7.0 Hz), 2.58–2.48 (1H, m), 1.77 (3H, d, J = 1.2 Hz), 1.30–1.20 (10H, m), 0.99 (3H, d, J = 6.5 Hz) and 0.90–0.82 (6H, m) |
| 6a | $C_{25}H_{36}O_6$ | m/z 432, M + <5% | LC-MS (thermospray) | CDCl$_3$ | 7.30 (1H, d, J = 15.7 Hz), 7.01 (1H, dd, J = 9.8, 5.4 Hz), 6.89 (1H, dd, J = 15.7, 4.8 Hz), 6.31 (1H, dd, J = 15.7, 1.8 Hz), 6.23 (1H, d, J = 9.8 Hz), 5.73 (1H, d, J = 15.4 Hz), 5.72 (1H, d, J = 10.0 Hz), 5.49 (1H, dd, J = 5.3, 3.4 Hz), 5.27–5.22 (1H, m), 4.12 (2H, t, J = 6.6 Hz), 2.58–2.48 (1H, m), 1.76 (3H, d, J = <1.0 Hz), 1.68 (2H, sextet, J = 7.3 Hz), 1.30–1.20 (10H, m), 0.98 (3H, d, J = 6.7 Hz), 0.94 (3H, t, J = 7.4 Hz) and 0.88 (3H, t, J = 6.9 Hz) |
| 6b | $C_{26}H_{38}O_6$ | m/z 446, M + <5% | LC-MS | CDCl$_3$ | 7.30 (1H, dd, J = 15.7, <1.0 Hz), 7.01 (1H, dd, J = 9.6, 5.2 Hz), 6.88 (1H, dd, J = 15.7, 4.6 Hz), 6.30 (1H, dd, J = 15.7, 1.6 Hz), 6.22 (1H, d, J = 9.8 Hz), 5.75–5.70 (2H, m), 5.49 (1H, dd, J = 5.3, 3.3 Hz), 5.26–5.22 (1H, m), 4.16 (2H, td, J = 6.7, <1.0 Hz), 2.57–2.47 (1H, m), 1.77 (3H, d, J < 1.0 Hz), 1.68–1.60 (2H, m), 1.45–1.20 (12H, m), 0.99 (3H, d, J = 6.7 Hz), 0.93 (3H, t, J = 7.4 Hz) and 0.88 (3H, t, J = 7.0 Hz) |
| 6c | $C_{29}H_{37}O_5N$ | m/z 480 (MH+, 62%) m/z 497 (M + NH$_4^+$, base peak) | DCI + NH$_3$ | CDCl$_3$ | 7.37–7.26 (5H, m), 7.01 (1H, dd, J = 9.8, 5.1 Hz), 6.88 (1H, dd, J = 15.2, 4.2 Hz), 6.29 (1H, dd, J = 15.2, 1.9 Hz), 6.21 (1H, d, J = 9.8 Hz), 5.90–5.80 (1H, m), 5.75–5.68 (2H, m), 5.51 (1H, dd, J = 5.1, 3.5 Hz), 5.27–5.24 (1H, m), 4.58–4.48 (2H, m), 2.58–2.47 (1H, m), 1.76 (3H, d, J < 1.0 Hz), 1.40–1.19 (10H, m), 0.98 (3H, d, J = 6.7 Hz) and 0.87 (3H, t, J = 7.0 Hz) |

What is claimed is:

1. A compound selected from the group consisting of a 5,6-dihydro-α-pyrone of formula (I):

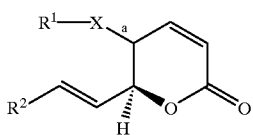

(I)

wherein bond a is oriented either ▶ or ▮▮▮;

X is O or NH;

R$^1$ is selected from the group consisting of:
    a group R$^3$(O)C— wherein R$^3$ is selected from the group consisting of: (i) a group of formula R$^4$—CH=CH— wherein R$^4$ is C$_1$–C$_{20}$ alkyl, C$_2$–C$_{20}$ alkenyl, an aryl group,
    or a 5- or 6-membered unsaturated heterocyclic ring containing one or two O, N or S atoms, (ii) C$_2$–C$_{20}$ alkyl;
    and (iii) an aryl group or a substituent which is a fused ring system of formula (1) or (2):

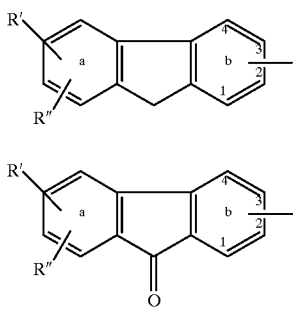
(1)

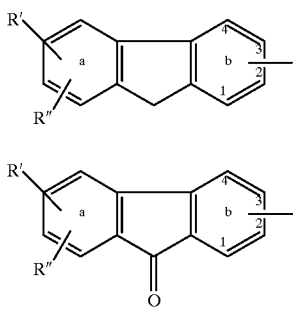
(2)

wherein each of R' and R", which are the same or different and may occupy any position on ring a or ring b of said fused ring system, is H or $C_1$–$C_6$ alkyl; a group $ArCH_2$— wherein Ar is an aryl group; and a group $R^5O$—$CH_2$— wherein $R^5$ is $C_1$–$C_6$ alkyl optionally interrupted by one or two O atoms; and $R^2$ is $CH_3$ or, when $R^1$ is a group of formula (A) as defined below, $R^2$ is $R^6OOC$— or $R^6NOC$— wherein $R^6$ is $C_1$–$C_6$ alkyl;

and the pharmaceutically and veterinarily acceptable salts and esters thereof; with the exception of compounds wherein bond a is oriented ▶;

X is O and $R^1$ is a group of formula (A):

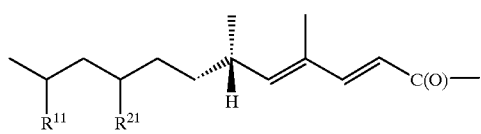
(A)

wherein $R^{11}$ and $R^{21}$ are H when $R^2$ in formula (I) is $CO_2H$ or $CH_3$, or one of $R^{11}$ and $R^{21}$ is H and the other is OH when $R^2$ in formula (I) is $CO_2H$.

2. A compound according to claim 1 wherein the 5,6-dihydro-α-pyrone has the formula (Ia):

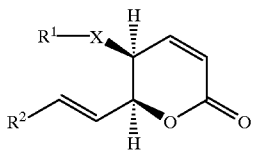
(Ia)

wherein

X is O and $R^1$ is a group $R^3(O)C$—, $ArCH_2$— or $R^5O$—$CH_2$— as defined in claim 1, or X is NH and $R^1$ is a group $R^3(O)C$— or $ArCH_2$ as defined in claim 1.

3. A compound according to claim 2 wherein, in formula (Ia), X is O and $R^1$ is selected from the group consisting of:

a group $R^3(O)C$— wherein $R^3$ is selected from the group consisting of: (a) a group of formula $R^4$—CH=CH— wherein $R^4$ is naphthyl, furanyl or a phenyl group which is unsubstituted or substituted by $C_1$–$C_6$ alkyl, halo, nitro or hydroxy; (b) a phenyl group which is unsubstituted or para-substituted by $C_1$–$C_6$ alkyl or by phenyl, which phenyl is in turn unsubstituted or substituted by $C_1$–$C_6$ alkyl or $OCOR^7$ in which $R^7$ is $C_1$–$C_{10}$ alkyl, or (c) a substituent of formula (1a), (2a) or (2b):

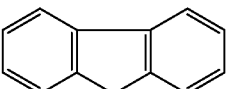
(1a)

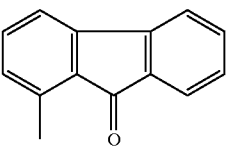
(2a)

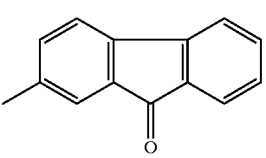
(2b)

and a group $ArCH_2$— wherein Ar is a phenyl group which is unsubstituted or substituted by para-phenyl, the said para-phenyl being unsubstituted or mono-substituted by $C_1$–$C_6$ alkyl or —$OCOR^7$ as defined above;

or X is NH and $R^1$ is a group $R^3(O)C$— wherein $R^3$ is a phenyl group substituted by para-phenyl, the said para-phenyl being unsubstituted or substituted by $C_1$–$C_6$ alkyl or —$OCOR^7$ as defined above.

4. A compound according to claim 1 wherein the 5,6-dihydro-α-pyrone has the formula (Ib):

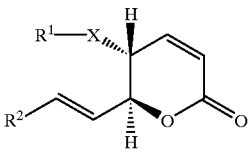
(Ib)

wherein

X is O and $R^1$ is a group $R^3(O)C$— as defined in claim 1, or X is —NH and $R^1$ is a group $R^3(O)C$— or $ArCH_2$— as defined in claim 1.

5. A compound according to claim 4 wherein, in formula (Ib), X is O and $R^1$ is a group $R^3(O)C$— wherein $R^3$ is a phenyl group which is unsubstituted or substituted by $C_1$–$C_6$ alkyl or —$OCOR^7$ wherein $R^7$ is $C_1$–$C_{10}$alkyl, or X is NH and $R^1$ is a group $R^3(O)C$— wherein $R^3$ is phenyl group which is unsubstituted or substituted by "phenyl, the said phenyl being in turn unsubstituted or substituted by $C_1$–$C_6$ alkyl or —$OCOR^7$ as defined above, or $R^3$ is a substituent of formula (1b):

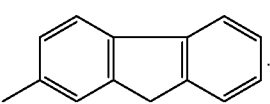
(1b)

6. A pharmaceutical or veterinary composition which comprises a pharmaceutically or veterinarily acceptable carrier or diluent and, as an active ingredient, a compound as defined in claim 1.

7. A compound selected from the group consisting of:
((2S,3R)-3,6-Dihydro-6-oxo-(2E-prop-1-enyl-2H-pyran-3-yl)) benzoate;
((2S,3R)-3,6-Dihydro-6-oxo-(2E-prop-1-enyl-2H-pyran-3-yl))-4-biphenyl carboxylate;
((2S,3R)-3,6-Dihydro-6-oxo-(2E-prop-1-enyl-2H-pyran-3-yl))-9-oxo-9H-fluorene carboxylate;
((2S,3R)-3,6-Dihydro-6-oxo-(2E-prop-1-enyl-2H-pyran-3-yl))-9-oxo-9H-fluorene-2-carboxylate;
(5S,6R)-5-benzylamino-6E-prop-1-ene-5,6-dihydro-2H-pyran-2-one;
(5S,6R)-5-(4-biphenylmethylamino)-6E-prop-1-ene-5,6-dihydro-2H-pyran-2-one;
(5S,6R)-5-(2-9H-fluorenemethylamino)-6E-prop-1-ene-5,6-dihydro-2H-pyran-2-one;
((2S,3R)-3,6-Dihydro-6-oxo-(2E-prop-1-enyl-2H-pyran-3-yl)) phenylamide;
((2S,3R)-3,6-Dihydro-6-oxo-(2E-prop-1-enyl-2H-pyran-3-yl))4-biphenylamide;
((2S,3R)-3,6-Dihydro-6-oxo-(2E-prop-1-enyl-2H-pyran-3-yl))-9-oxo-9H-fluorene-4-amide;
((2S,3R)-3,6-Dihydro-6-oxo-(2E-prop-1-enyl-2H-pyran-3-yl))-4-biphenylamide;
((2S,3R)-3,6-Dihydro-6-oxo-(2E-prop-1-enyl-2H-pyran-3-yl))-9-oxo-9H-fluorene-4-amide;
((2S,3R)-3,6-Dihydro-6-oxo-(2E-prop-1-enyl-2H-pyran-3-yl))-4-biphenylamide;
((2S,3R)-3,6-Dihydro-6-oxo-(2E-prop-1-enyl-2H-pyran-3-yl))2-fluorene-4-amide;
((2S,3R)-3,6-Dihydro-6-oxo-(2E-prop-1-enyl-2H-pyran-3-yl))-(2E,4E)-4,6-dimethyldodecanoate;
(2S,3S)-5-(2-Methoxy-ethoxymethoxy)-6-(2E-prop-1-enyl)-5,6-dihydro-2H-pyran-2-one;
(2S,3S)-5-(4-Biphenylmethoxy)-6-(2E-prop-1-enyl)-5,6-dihydro-2H-pyran-2-one;
(2S,3S)-5-Benzyloxy-6-(2E-prop-1-enyl)-S,6-dihydro-2H-pyran-2-one;
((2S,3S)-3,6-Dihydro-6-oxo-(2E-prop-1-enyl-2H-pyran-3-yl))dodeca-2E-enoate;
((2S,3S)-3,6-Dihydro-6-oxo-(2E-prop-1-enyl-2H-pyran-3-yl))-3-(2-furfuryl)acrylate;
((2S,3S)-3,6-Dihydro-6-oxo-(2E-prop-1-enyl-2H-pyran-3-yl))-4-biphenylcarboxylate;
((2S,3S)-3,6-Dihydro-6-oxo-(2E-prop-1-enyl-2H-pyran-3-yl))-4'-ethyl-4-biphenylcarboxylate;
((2S,3S)-3,6-Dihydro-6-oxo-(2E-prop-1-enyl-2H-pyran-3-yl))-9H-fluorenecarboxylate;
((2S,3S)-3,6-Dihydro-6-oxo-(2E-prop-1-enyl-2H-pyran-3-yl))-9-oxo-9H-fluorene carboxylate;
((2S,3S)-3,6-Dihydro-6-oxo-(2E-prop-1-enyl-2H-pyran-3-yl))-9-oxo-9H-fluorene-2-carboxylate;
((2S,3S)-3,6-Dihydro-6-oxo-(2E-prop-1-enyl-2H-pyran-3-yl))-4-biphenylacetate;
((2S,3S)-3,6-Dihydro-6-oxo-(2E-prop-1-enyl-2H-pyran-3-yl))phenylacetate;
((2S,3S)-3,6-Dihydro-6-oxo-(2E-prop-1-enyl-2H-pyran-3-yl))-3m-tolylacrylate;
((2S,3S)-3,6-Dihydro-6-oxo-(2E-prop-1-enyl-2H-pyran-3-yl))-3-(2-naphthyl)acrylate;
((2S,3S)-3,6-Dihydro-6-oxo-(2E-prop-1-enyl-2H-pyran-3-yl))-4-pentylbenzoate;
((2S,3S)-3,6-Dihydro-6-oxo-(2E-prop-1-enyl-2H-pyran-3-yl))dodecanoate;
((2S,3S)-3,6-Dihydro-6-oxo-(2E-prop-1-enyl-2H-pyran-3-yl))tetradodecanoate;
((2S,3S)-3,6-Dihydro-6-oxo-(2E-3-oxo-3-ethoxyprop-1-enyl-2H-pyran-3-yl))-(2E,4E)-4,6-dimethyldodecadienoate;
((2S,3S)-3,6-Dihydro-6-oxo-(2E-3-oxo-3-propoxyprop-1-enyl)-2H-pyran-3-yl)-(2E,4E)-4,6-dimethyldodecadienoate;
((2S,3S)-3,6-Dihydro-6-oxo-(2E-3-oxo-3-butoxyprop-1-enyl)-2H-pyran-3-yl)-(2E,4E)-4,6-dimethyldodecadienoate;
and((2S,3S)-3,6-Dihydro-6-oxo-(2E-3-oxo-3-benzylaminoprop-1-enyl)-2H-pyran-3-yl)-(2E,4E)-4,6-dimethyldodecadienoate;
and the pharmaceutically and veterinarily acceptable salts thereof.

8. A pharmaceutical or veterinary composition which comprises a pharmaceutically or veterinarily acceptable carrier or diluent and, as an active ingredient, a compound as defined in claim 7.

9. A process for producing a compound as defined in claim 1, which process comprises the steps of:

a) esterifying a compound of formula (II)

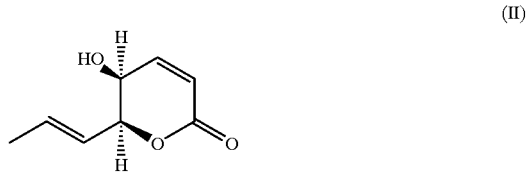

(II)

or of formula (IIa):

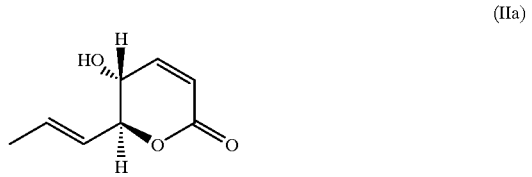

(IIa)

with a carboxylic acid of formula (III):

R³—COOH      (III)

wherein R³ is as defined in claim 1; or (b) treating a compound of formula (IV):

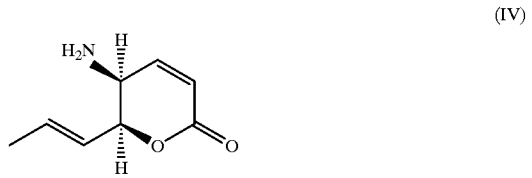

(IV)

or of formula (IVa):

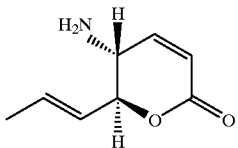

(IVa)

with an aldehyde of formula ArCHO wherein Ar is aryl, or c) treating a compound of formula (IV) or (IVa) as defined above with an acid chloride of formula $R^3$—COCl wherein $R^3$ is as defined in claim 1, or d) treating a compound of formula (II) or (IIa) as defined above with a halo compound of formula (V):

Ar—CH$_2$Y  (V)

wherein Ar is aryl and Y is a halogen, or a halo compound of formula (VI):

$R^5$OCH$_2$Y  (VI)

wherein $R^5$ is as defined in claim 1 and Y is a halogen; and e) if desired, converting a resulting 5,6-dihydro-α-pyrone into a pharmaceutically acceptable salt thereof.

10. A method for the treatment of a patient in need of a cytokine production inhibitor, which method comprises administering thereto a therapeutically effective amount of a compound as defined in claim 1.

11. A method for the treatment of a patient in need of an IL-1 production inhibitor, which method comprises administering thereto a therapeutically effective amount of a compound as defined in claim 1.

12. A method for the treatment of an immunoinflammatory condition, which method comprises administering to a patient in need thereof a therapeutically effective amount of a compound as defined in claim 1.

13. A method according to claim 12 wherein the immunoinflammatory condition is selected from the group consisting of rheumatoid arthritis, osteoarthritis, septic shock, psoriasis, atherosclerosis, inflammatory bowel disease, Crohn's disease and asthma.

* * * * *